(12) United States Patent
Harashima et al.

(10) Patent No.: US 8,809,495 B2
(45) Date of Patent: Aug. 19, 2014

(54) PEPTIDES IMPARTING CELL PERMEABILITY TO LIPID MEMBRANE STRUCTURE AND/OR ENHANCING CELL PERMEABILITY OF LIPID MEMBRANE STRUCTURE, AND LIPID MEMBRANE STRUCTURE COMPRISING LIPID BOUND TO SUCH PEPTIDE AS CONSTITUENT LIPID AND HAVING CELL PERMEABILITY OR SHOWING ENHANCED CELL PERMEABILITY

(75) Inventors: Hideyoshi Harashima, Sapporo (JP); Takahiro Fujiwara, Sapporo (JP); Hidetaka Akita, Sapporo (JP)

(73) Assignee: National University Corporation Hokkaido University, Sapporo-Shi (JP)

( * ) Notice: Subject to any disclaimer, the term of this patent is extended or adjusted under 35 U.S.C. 154(b) by 0 days.

(21) Appl. No.: 13/515,970

(22) PCT Filed: Dec. 14, 2010

(86) PCT No.: PCT/JP2010/072485
§ 371 (c)(1), (2), (4) Date: Aug. 16, 2012

(87) PCT Pub. No.: WO2011/074578
PCT Pub. Date: Jun. 23, 2011

(65) Prior Publication Data
US 2012/0309937 A1 Dec. 6, 2012

(30) Foreign Application Priority Data
Dec. 14, 2009 (JP) .................. 2009-283091

(51) Int. Cl.
C07K 7/06 (2006.01)
A61K 47/42 (2006.01)
A61K 9/127 (2006.01)
C07K 14/47 (2006.01)
A61K 38/00 (2006.01)
A61K 39/00 (2006.01)

(52) U.S. Cl.
CPC .. *C07K 7/06* (2013.01); *A61K 47/42* (2013.01)
USPC ........................................ 530/300

(58) Field of Classification Search
CPC .......... C07K 7/06; C07K 14/47; A61K 47/42; A61K 9/127
USPC ........................................ 530/300
See application file for complete search history.

(56) References Cited

U.S. PATENT DOCUMENTS

| 6,017,882 A | * | 1/2000 | Nelsestuen | ............... 514/14.9 |
| 2008/0241917 A1 | | 10/2008 | Akita et al. | |
| 2009/0285780 A1 | * | 11/2009 | Lee | ............... 424/85.4 |

FOREIGN PATENT DOCUMENTS

| JP | 11-512451 | 10/1999 |
| JP | 2001-517436 | 10/2001 |
| JP | 2007-526227 | 9/2007 |
| JP | 2008-31142 | 2/2008 |
| JP | 2008031142 A * | 2/2008 |
| WO | WO 97/10850 | 3/1997 |
| WO | WO 99/15649 | 4/1999 |
| WO | WO 2005/002515 A2 | 1/2005 |
| WO | WO 2007/037444 A1 | 4/2007 |
| WO | WO 2007107156 A2 * | 9/2007 |

OTHER PUBLICATIONS

JP 2008031142 A1, published Feb. 14, 2008, machine translation of the specification, provided by Japan Patent Office, Paten & Utility Model Gazette DB, at http://www4.ipdl.inpit.go.jp/Tokujitu/tjsogodbenk.ipdl (accessed Jan. 9, 2013).*
Hobert et al., "The cytoplasmic juxtamembrane domain of the epidermal growth factor receptor contains a novel autonomous basolateral sorting determinant", J. Biol. Chem. 272(52):32901-32909 (1997).*
Harashima et al., J Pharm. Society of Japan. 127:1655-72 (2007).
Lu et al., J Controlled Release. 110:505-13 (2006).
Woodle and Lasic, Biochimica et Biophysica Acta. 1113:171-99 (1992).
PCT/JP2010/072485 International Search Report by Japanese Patent Office dated Mar. 15, 2011.

* cited by examiner

*Primary Examiner* — Christina Bradley
*Assistant Examiner* — Kristina M Hellman
(74) *Attorney, Agent, or Firm* — RatnerPrestia

(57) ABSTRACT

Provided are peptides imparting cell permeability to a lipid membrane structure and/or enhancing the cell permeability of a lipid membrane structure, and a lipid membrane structure which comprises, as a constituent lipid, a lipid bound to such a peptide and has cell permeability or shows enhanced cell permeability. The amino acid sequences of the peptides imparting cell permeability to a lipid membrane structure and/or enhancing the cell permeability of a lipid membrane structure are represented by: $LX_1X_2X_1X_1X_1L$, $LLX_2X_1X_1X_1L$ and $LX_1X_2X_1X_1L$ (wherein L represents a leucine residue; $X_1$ represents a polar amino acid residue; and $X_2$ represents a polar, non-charged and branched chain amino acid residue).

16 Claims, 18 Drawing Sheets

PEPTIDES IMPARTING CELL PERMEABILITY TO LIPID MEMBRANE STRUCTURE AND/OR ENHANCING CELL PERMEABILITY OF LIPID MEMBRANE STRUCTURE, AND LIPID MEMBRANE STRUCTURE COMPRISING LIPID BOUND TO SUCH PEPTIDE AS CONSTITUENT LIPID AND HAVING CELL PERMEABILITY OR SHOWING ENHANCED CELL PERMEABILITY

CROSS REFERENCE TO RELATED APPLICATIONS

This is a U.S. National Application of International Application PCT/JP2010/072485, filed Dec. 14, 2010, which claims priority to Japanese Application No. 2009-283091, filed Dec. 14, 2009, the contents of each of which are incorporated by reference in their entireties for all purposes.

FIELD OF THE INVENTION

The present invention relates to peptides imparting cell permeability to a lipid membrane structure and/or enhancing the cell permeability of a lipid membrane structure, and a lipid membrane structure comprising, as a constituent lipid, a lipid bound to such a peptide and having cell permeability or showing enhanced cell permeability.

BACKGROUND OF THE INVENTION

Vectors or carriers are actively developed for positively delivering substances such as proteins, agents, or nucleic acids to target sites in individual organisms. For example, viral vectors such as a retrovirus, an adenovirus, and an adeno-associated virus have each been developed as a vector for introducing a gene of interest into target cells. However, viral vectors have problems such as difficult large-scale production, antigenicity, and toxicity; thus, attention has been drawn to a lipid membrane structure typified by a liposome vector and a peptide carrier which have such problems reduced.

The liposome vector is a lipid membrane structure using an artificially prepared lipid bilayer membrane as a basic configuration and has the ability to encapsulate various substances for delivery into target cells. The liposome vector has the advantage of encapsulating a substance and thereby protecting it from in vivo decomposition or metabolism and the advantage of preventing the substance from acting at sites other than a target site (side effects) in addition to the advantage of being improved in tropism for a target site by introducing a functional molecule such as an antibody, a protein, or a sugar chain into the surface thereof.

When a high-molecular compound such as a lipid membrane structure encapsulating a substance such as a protein, an agent, or a nucleic acid or a peptide carrier binding to a protein, an agent, a nucleic acid, or the like is administered into the blood, however, it represents a big challenge to cause the compound to reach from the blood to a target site. Vascular endothelial cells form tight junction between the cells in many tissues and the gap between vascular endothelial cells is as very narrow as about 0.4 nm to about 4 nm; thus, it is difficult for the high-molecular compound administered into the blood to reach the target site through the gap.

Accordingly, lipid membrane structures or peptide carriers are researched and developed which each reach the target site across a vascular endothelial cell layer forming tight junction; for example, the development has been performed of a peptide promoting transcytosis in epithelial cells, selected from albumin, GP60 as an albumin-binding protein, and an anti-GP60 antibody (Patent Literature 1), a peptide promoting transcytosis in the blood-brain barrier, comprising the binding part of megalin as an endocytosis receptor (Patent Literature 2), a method involving co-administrating an antisense oligonucleotide inhibiting the synthesis of occludin as a tight junction-forming protein and a lipid membrane structure or a peptide carrier (Patent Literature 3), and the like.

CITATION LIST

Patent Literature

Patent Literature 1
National Publication of Japanese Patent Application No. 11-512451
Patent Literature 2
National Publication of Japanese Patent Application No. 2007-526227
Patent Literature 3
National Publication of Japanese Patent Application No. 2001-517436

SUMMARY OF THE INVENTION

However, each of the peptides promoting transcytosis described in Patent Literatures 1 and 2 is a peptide carrier directly binding to an agent and does not provide a lipid membrane structure having cell permeability. The method described in Patent Literature 3 risks to cause the leakage of vascular contents other than a desired substance with the breakdown of the tight junction.

The present invention has been made to solve such problems and has an object of providing peptides imparting cell permeability to a lipid membrane structure and/or enhancing the cell permeability of a lipid membrane structure, and a lipid membrane structure comprising, as a constituent lipid, a lipid bound to such a peptide and having cell permeability or showing enhanced cell permeability.

As a result of intensive studies, the present inventors have found that a peptide having an amino acid sequence of the following: $LX_1X_2X_1X_1X_1L$, $LLX_2X_1X_1X_1L$, or $LX_1X_2X_1X_1L$, wherein L represents a leucine residue; $X_1$ represents a polar amino acid residue; and $X_2$ represents a polar, non-charged and branched chain amino acid residue, imparts cell permeability to a lipid membrane structure and enhances the cell permeability of a lipid membrane structure in epithelial cells, thereby accomplishing the following inventions.

(1) A peptide having an amino acid sequence of the following: $LX_1X_2X_1X_1X_1L$, $LLX_2X_1X_1X_1L$, or $LX_1X_2X_1X_1L$, wherein L represents a leucine residue; $X_1$ represents a polar amino acid residue; and $X_2$ represents a polar, non-charged and branched chain amino acid residue, imparting cell permeability to a lipid membrane structure and/or enhancing the cell permeability of a lipid membrane structure.

(2) The peptide according to (1), wherein the polar, non-charged and branched chain amino acid residue $X_2$ is Q, wherein Q represents a glutamine residue.

(3) The peptide according to (1) or (2), wherein the polar amino acid residues $X_1$ are the same or different amino acid residues selected from the group consisting of R, K, S, and D, wherein R represents an arginine residue; K represents a lysine residue; S represents a serine residue; and D represents an aspartic acid residue.

(4) The peptide according to any of (1) to (3), wherein the amino acid sequence is LRQRRRL (SEQ ID NO: 1), LLQRRRL (SEQ ID NO: 14), LRQRRL (SEQ ID NO: 26), LKQKKKL (SEQ ID NO: 15), LLQKKKL (SEQ ID NO: 38), LKQKKL (SEQ ID NO: 39), LRQSSSL (SEQ ID NO: 35), LLQSSSL (SEQ ID NO: 40), LRQSSL (SEQ ID NO: 41), LRQRDDL (SEQ ID NO: 37), LLQRDDL (SEQ ID NO: 42), or LRQRDL (SEQ ID NO: 43), wherein L represents a leucine residue; R represents an arginine residue; Q represents a glutamine residue; K represents a lysine residue; S represents a serine residue; and D represents an aspartic acid residue.

(5) The peptide according to any of (1) to (4), wherein the cell is an epithelial cell.

(6) The peptide according to any of (1) to (5), wherein the peptide is incorporated into cells via heparan sulfate proteoglycan present in lipid raft.

(7) A lipid membrane structure comprising, as a constituent lipid, a lipid bound to the peptide according to any of (1) to (6) and having cell permeability or showing enhanced cell permeability.

(8) The lipid membrane structure according to (7), wherein the lipid bound to the peptide is a lipid bound to a peptide in which a tyrosine residue, a cysteine residue, a hydrophilic polymer, and the lipid are bound in that order to the C-terminal end of the peptide.

(9) The lipid membrane structure according to (8), wherein the hydrophilic polymer is polyethylene glycol.

(10) The lipid membrane structure according to any of (7) to (9), wherein the percentage P of the lipid bound to the peptide in the total amount of constituent lipids is 1 mol %≤P≤10 mol %.

(11) The lipid membrane structure according to any of (7) to (10), wherein the cell is an epithelial cell.

(12) The lipid membrane structure according to any of (7) to (11), wherein the lipid membrane structure can be incorporated into cells via heparan sulfate proteoglycan present in lipid raft.

(13) An agent imparting cell permeability to and/or enhancing the cell permeability of a lipid membrane structure, comprising, as an active ingredient, a peptide having an amino acid sequence of the following: $LX_1X_2X_1X_1X_1L$, $LLX_2X_1X_1X_1L$, or $LX_1X_2X_1X_1L$, wherein L represents a leucine residue; $X_1$ represents a polar amino acid residue; and $X_2$ represents a polar, non-charged and branched chain amino acid residue.

(14) The agent imparting cell permeability and/or enhancing the cell permeability according to (13), wherein the polar, non-charged and branched chain amino acid residue $X_2$ is Q, wherein Q represents a glutamine residue.

(15) The agent imparting cell permeability and/or enhancing the cell permeability according to (13) or (14), wherein the polar amino acid residues $X_1$ are the same or different amino acid residues selected from the group consisting of R, K, S, and D, wherein R represents an arginine residue; K represents a lysine residue; S represents a serine residue; and D represents an aspartic acid residue.

(16) The agent imparting cell permeability and/or enhancing the cell permeability according to any of (13) to (15), wherein the amino acid sequence is LRQRRRL (SEQ ID NO: 1), LLQRRRL (SEQ ID NO: 14), LRQRRL (SEQ ID NO: 26), LKQKKKL (SEQ ID NO: 15), LLQKKKL (SEQ ID NO: 38), LKQKKL (SEQ ID NO: 39), LRQSSSL (SEQ ID NO: 35), LLQSSSL (SEQ ID NO: 40), LRQSSL (SEQ ID NO: 41), LRQRDDL (SEQ ID NO: 37), LLQRDDL (SEQ ID NO: 42), or LRQRDL (SEQ ID NO: 43), wherein L represents a leucine residue; R represents an arginine residue; Q represents a glutamine residue; K represents a lysine residue; S represents a serine residue; and D represents an aspartic acid residue.

(17) The agent imparting cell permeability and/or enhancing the cell permeability according to any of (13) to (16), wherein the cell is an epithelial cell.

(18) The agent imparting cell permeability and/or enhancing the cell permeability according to any of (13) to (17), wherein the peptide is a peptide capable of being incorporated into cells via heparan sulfate proteoglycan present in lipid raft.

(19) A method for producing a lipid membrane structure having cell permeability or showing enhanced cell permeability, comprising the step of modifying a lipid membrane structure with a peptide having an amino acid sequence of the following: $LX_1X_2X_1X_1X_1L$, $LLX_2X_1X_1X_1L$, or $LX_1X_2X_1X_1L$, wherein L represents a leucine residue; $X_1$ represents a polar amino acid residue; and $X_2$ represents a polar, non-charged and branched chain amino acid residue.

(20) The method according to (19), wherein the polar, non-charged and branched chain amino acid residue $X_2$ is Q, wherein Q represents a glutamine residue.

(21) The method according to (19) or (20), wherein the polar amino acid residues $X_1$ are the same or different amino acid residues selected from the group consisting of R, K, S, and D, wherein R represents an arginine residue; K represents a lysine residue; S represents a serine residue; and D represents an aspartic acid residue.

(22) The method according to any of (19) to (21), wherein the amino acid sequence is LRQRRRL (SEQ ID NO: 1), LLQRRRL (SEQ ID NO: 14), LRQRRL (SEQ ID NO: 26), LKQKKKL (SEQ ID NO: 15), LLQKKKL (SEQ ID NO: 38), LKQKKL (SEQ ID NO: 39), LRQSSSL (SEQ ID NO: 35), LLQSSSL (SEQ ID NO: 40), LRQSSL (SEQ ID NO: 41), LRQRDDL (SEQ ID NO: 37), LLQRDDL (SEQ ID NO: 42), or LRQRDL (SEQ ID NO: 43), wherein L represents a leucine residue; R represents an arginine residue; Q represents a glutamine residue; K represents a lysine residue; S represents a serine residue; and D represents an aspartic acid residue.

(23) The method according to any of (19) to (22), wherein the step of modifying a lipid membrane structure with a peptide is the step of modifying the lipid membrane structure with the peptide by binding a tyrosine residue, a cysteine residue, a hydrophilic polymer, and the lipid in that order to the C-terminal end of the peptide.

(24) The method according to any of (19) to (23), wherein the cell is an epithelial cell.

(25) The method according to (19) to (24), wherein the peptide is a peptide capable of being incorporated into cells via heparan sulfate proteoglycan present in lipid raft.

The binding of the peptide of the present invention or the use of the agent imparting cell permeability and/or enhancing the cell permeability according to the present invention can impart excellent cell permeability to and enhancing cell permeability of a lipid membrane structure. The lipid membrane structure comprising a lipid bound to the peptide of the present invention as a constituent lipid can reach a target site by passing through cells and release inclusions thereof; thus, it can be used as an excellent drug vector providing a high drug efficacy at the target site, having high safety, and easy to mass-produce.

PEG, RI/3-PEG, RI/4-PEG, RI/5-PEG, or RI/6-PEG), a liposome modified with PEG (RI/PEG or RI/800PEG), and a liposome modified with a peptide (RI/1 or RI/7). In the figure, RI/6-PEG, RI-PEG, RI/800PEG, and RI/7 shown by open columns indicate comparative examples.

Figure 2:
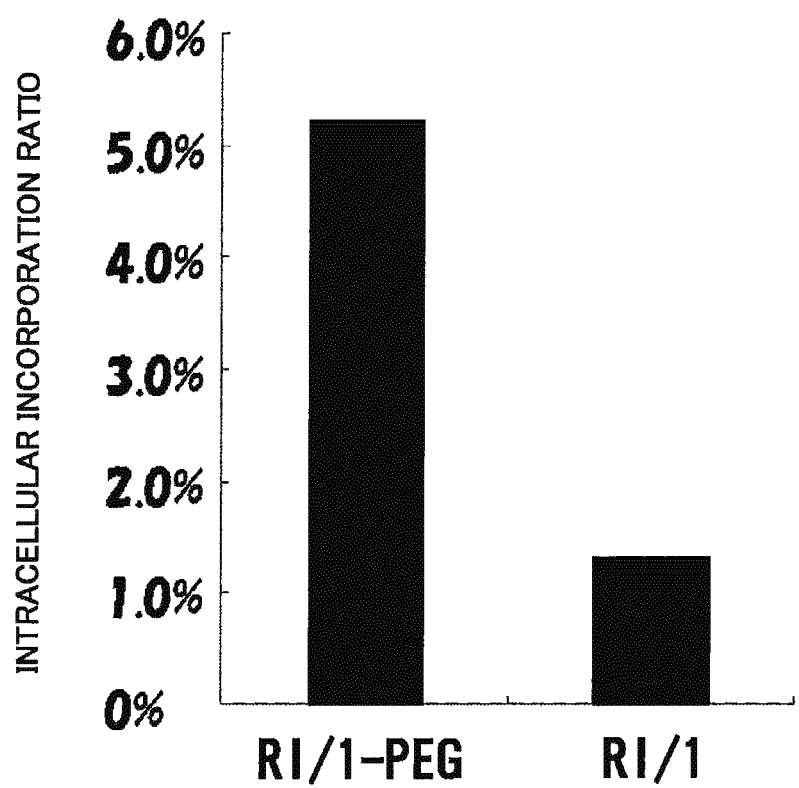

FIG. 2 is a graph showing the intracellular incorporation ratios of a liposome modified with a peptide 1 via PEG (RI/1-PEG) and a liposome modified with the peptide 1 not via PEG (RI/1).

Figure 3:
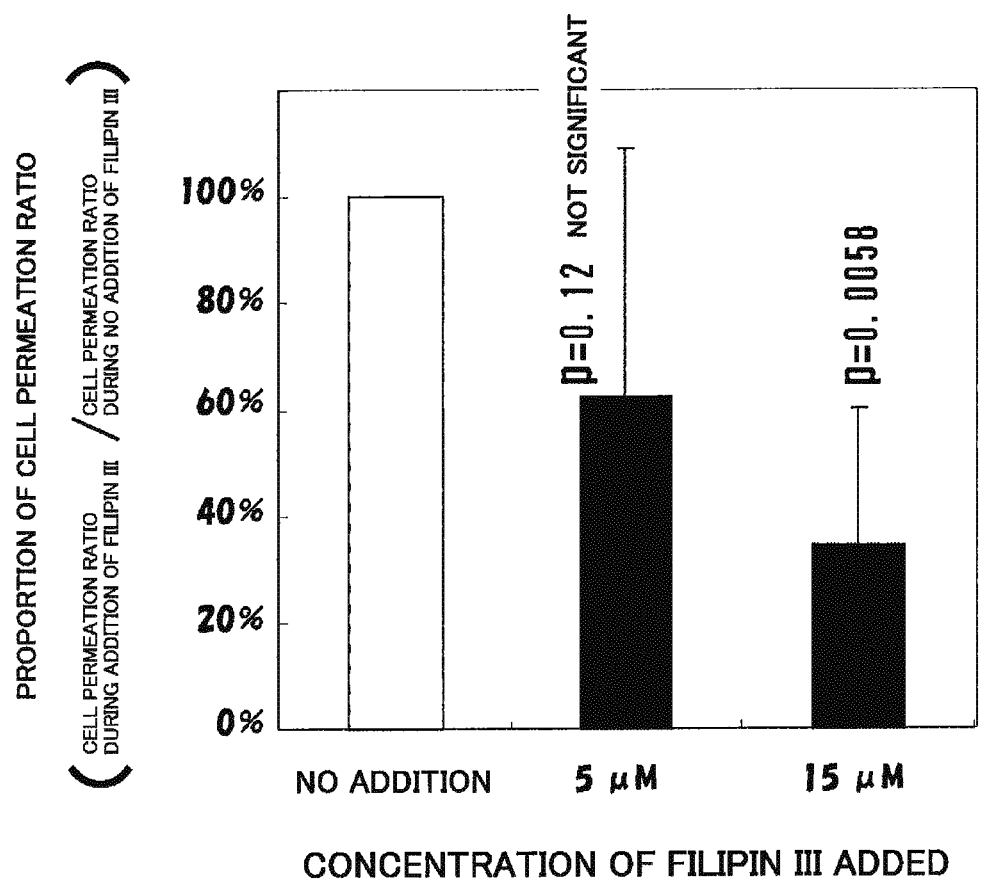

FIG. 3 is a graph showing the proportion of the cell permeation ratio of RI/1-PEG when Filipin III was added to inhibit the function of lipid raft to the ratio when Filipin III was not added.

Figure 4:
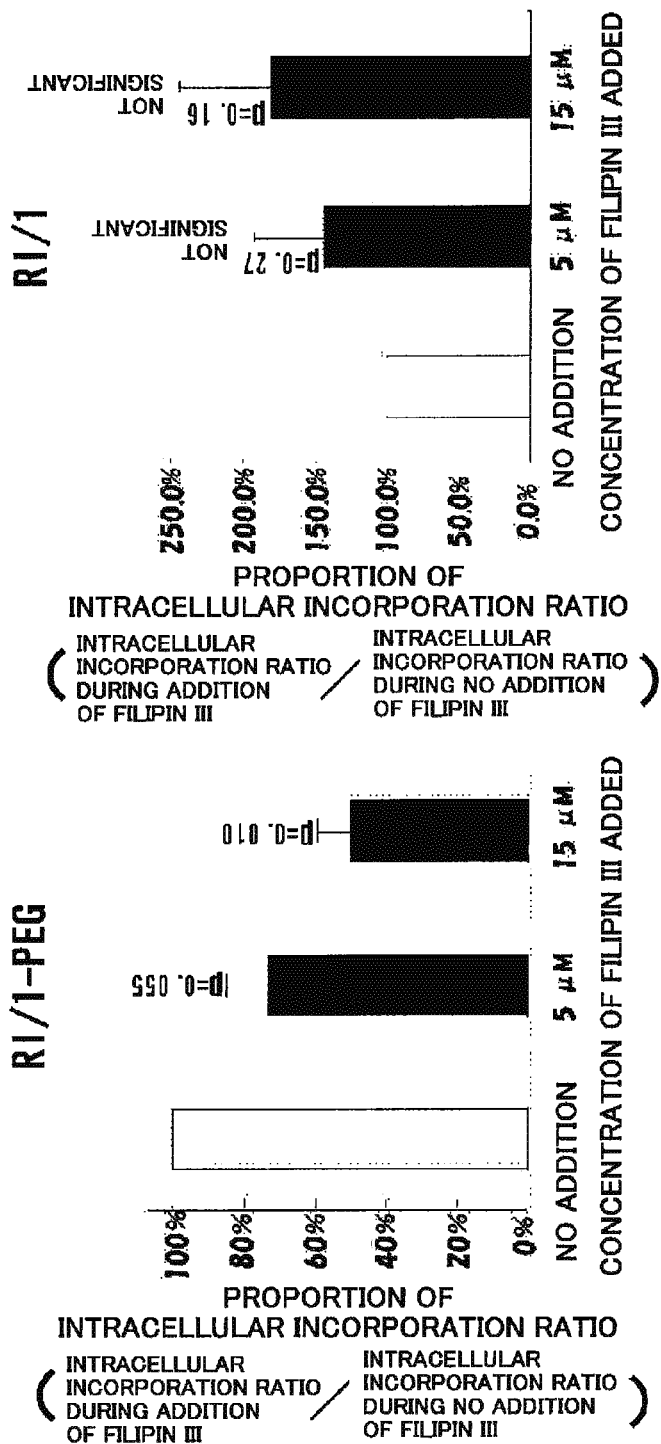

FIG. 4 is a graph showing the proportions of the cellular incorporation ratios of RI/1-PEG and RI/1 when Filipin III was added to inhibit the function of lipid raft to the ratios when Filipin III was not added.

Figure 5:
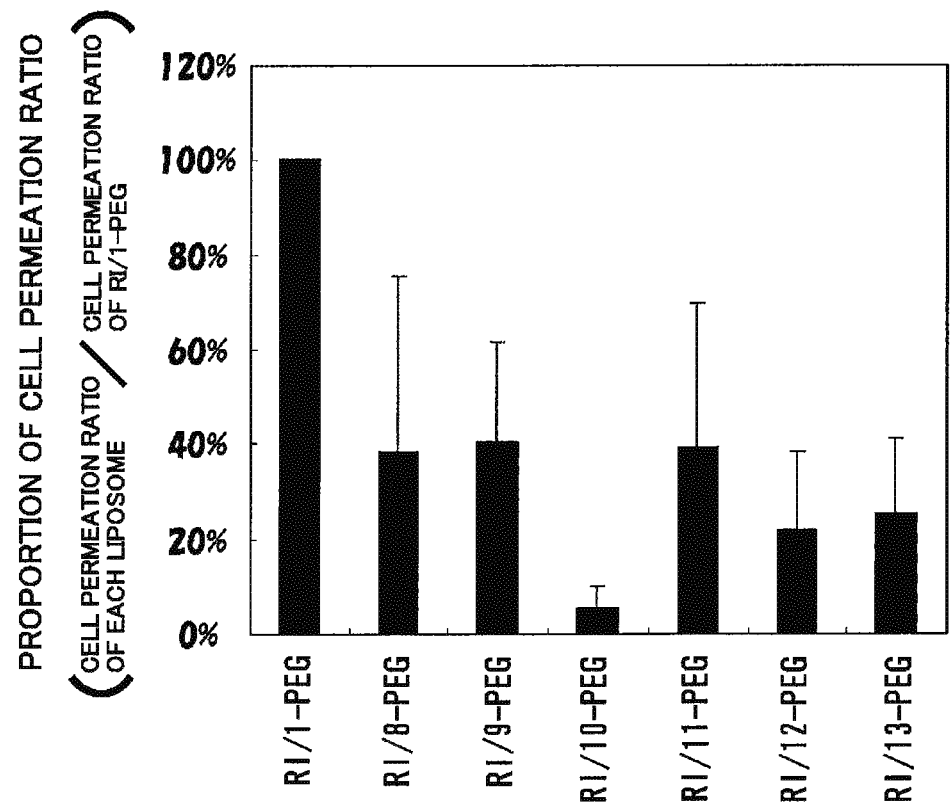

FIG. 5 is a graph showing the proportions of the cell permeation ratios of RI/8-PEG, RI/9-PEG, RI/10-PEG, RI/11-PEG, RI/12-PEG, and RI/13-PEG, assuming a cell permeation ratio of RI/1-PEG of 100(%).

Figure 6:
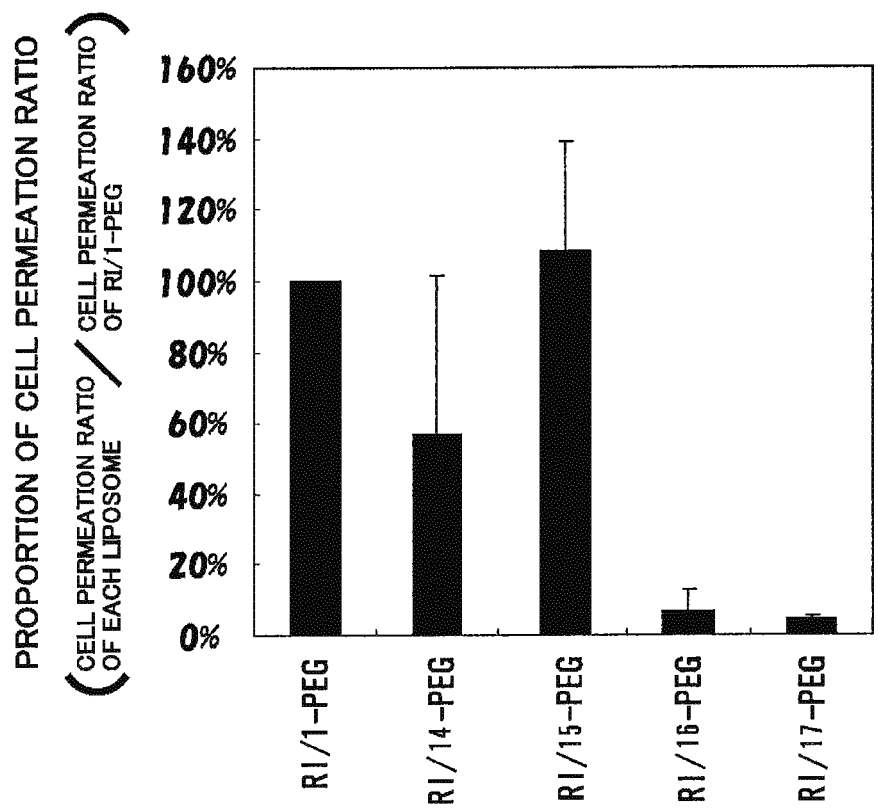

FIG. 6 is a graph showing the proportions of the cell permeation ratios of RI/14-PEG, RI/15-PEG, RI/16-PEG, and RI/17-PEG, assuming a cell permeation ratio of RI/1-PEG of 100(%).

Figure 7:
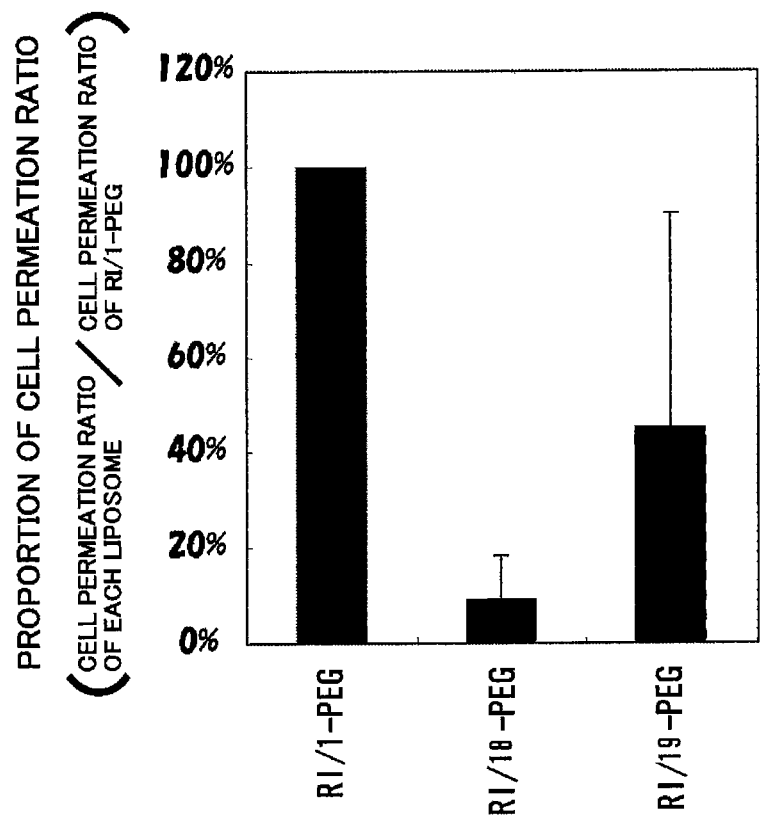

FIG. 7 is a graph showing the proportions of the cell permeation ratios of RI/18-PEG and RI/19-PEG, assuming a cell permeation ratio of RI/1-PEG of 100(%).

Figure 8:
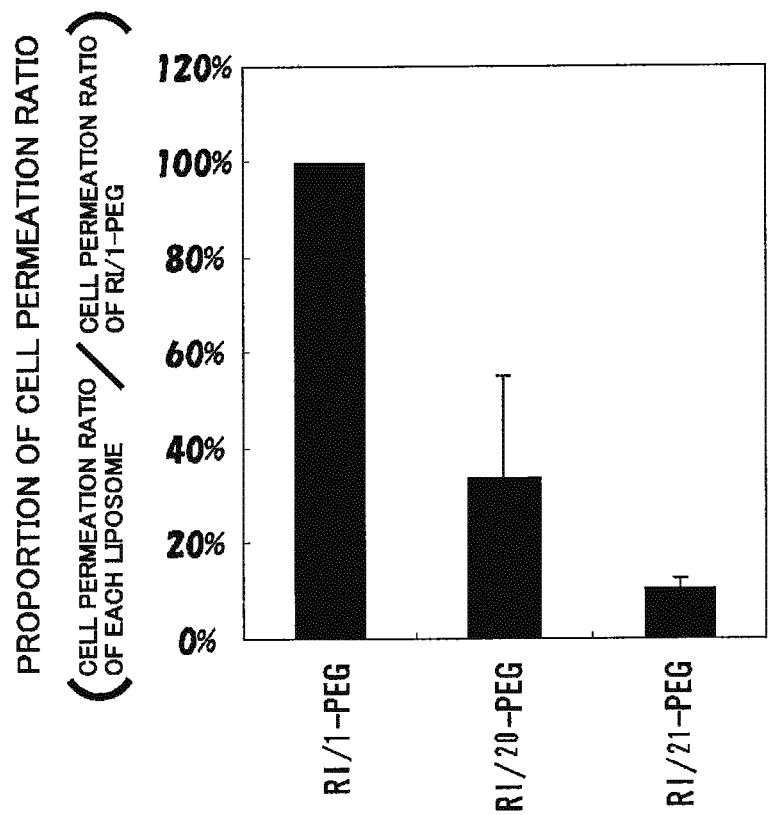

FIG. 8 is a graph showing the proportions of the cell permeation ratios of RI/20-PEG and RI/21-PEG, assuming a cell permeation ratio of RI/1-PEG of 100(%).

Figure 9:
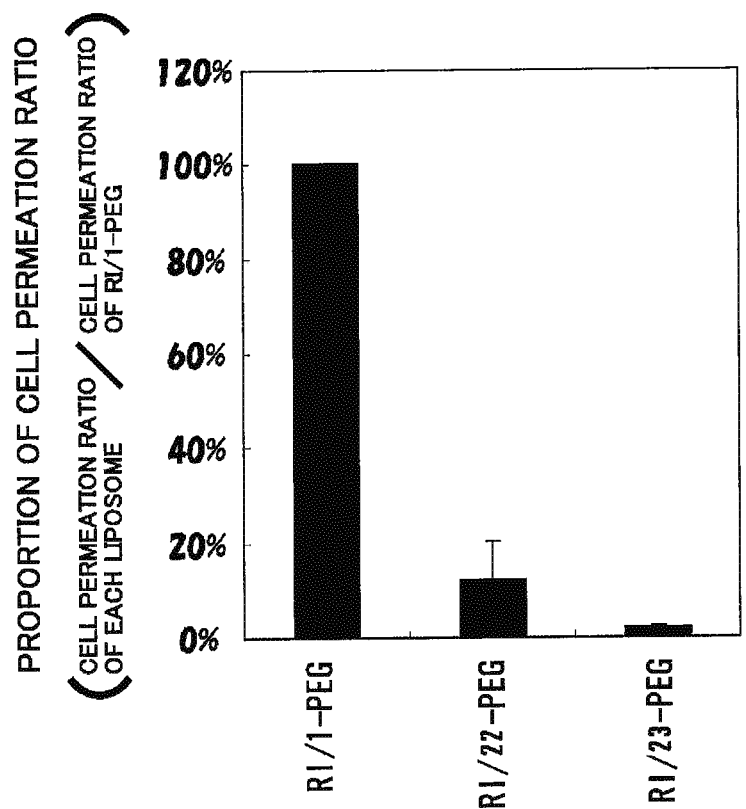

FIG. 9 is a graph showing the proportions of the cell permeation ratios of RI/22-PEG and RI/23-PEG, assuming a cell permeation ratio of RI/1-PEG of 100(%).

Figure 10:
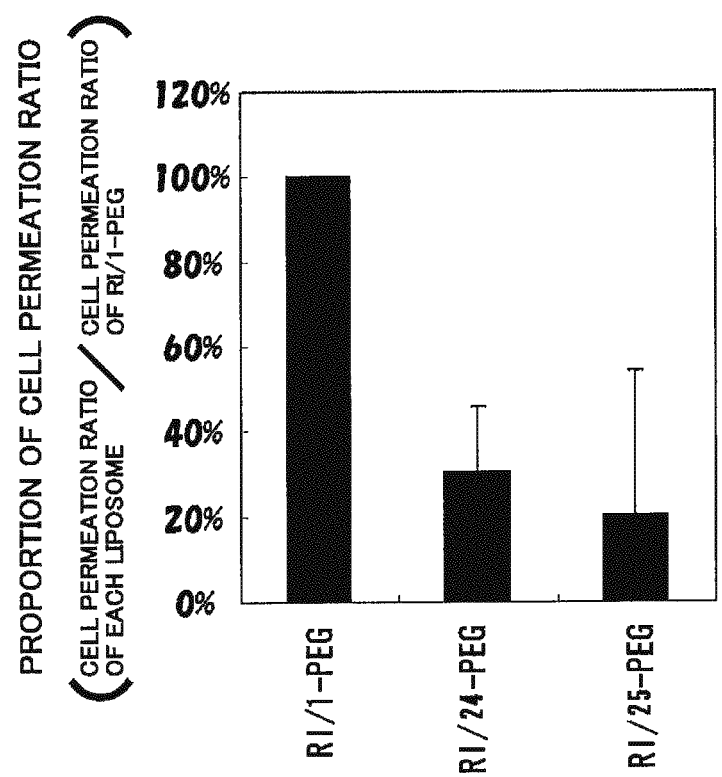

FIG. 10 is a graph showing the proportions of the cell permeation ratios of RI/24-PEG and RI/25-PEG, assuming a cell permeation ratio of RI/1-PEG of 100(%).

Figure 11:
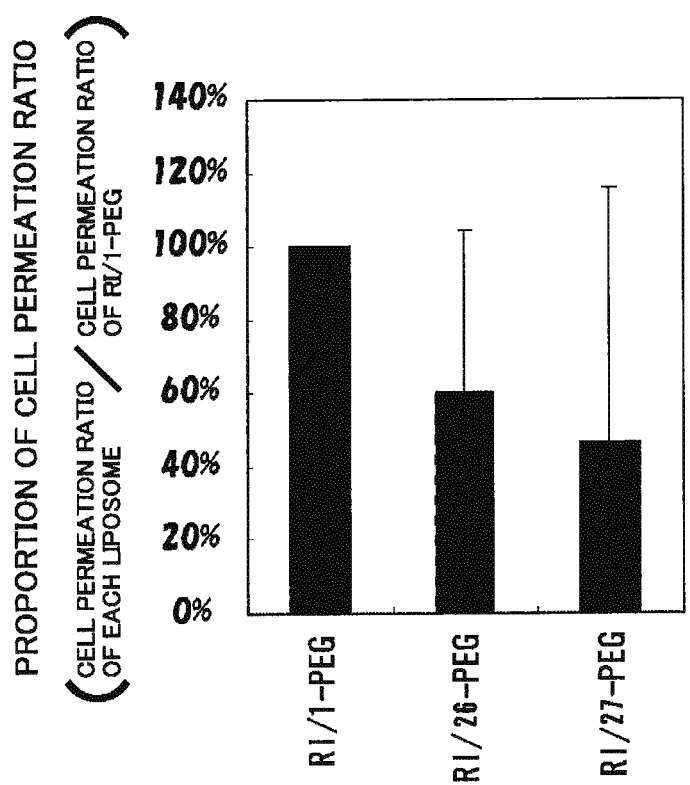

FIG. 11 is a graph showing the proportions of the cell permeation ratios of RI/26-PEG and RI/27-PEG, assuming a cell permeation ratio of RI/1-PEG of 100(%).

Figure 12:
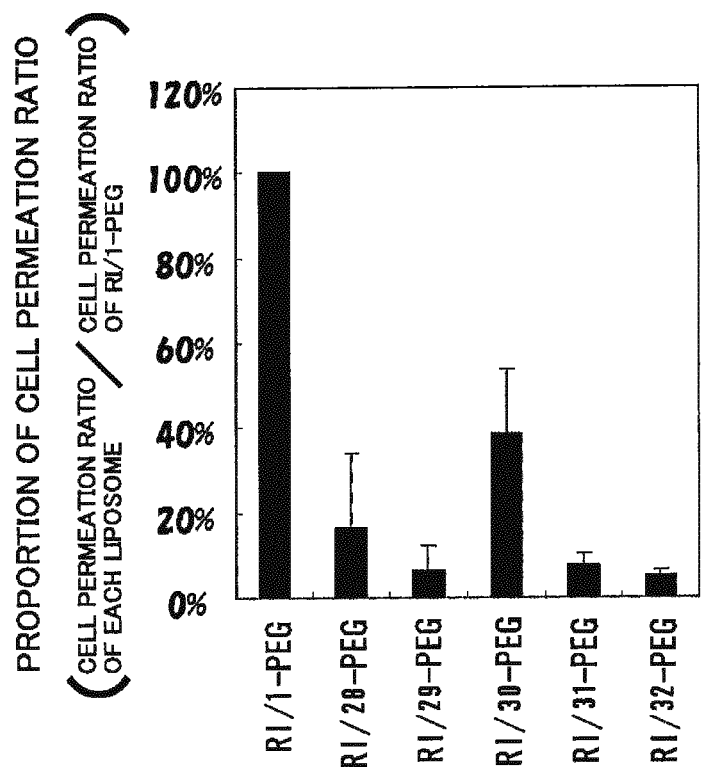

FIG. 12 is a graph showing the proportions of the cell permeation ratios of RI/28-PEG, RI/29-PEG, RI/30-PEG, RI/31-PEG, and RI/32-PEG, assuming a cell permeation ratio of RI/1-PEG of 100(%).

Figure 13:
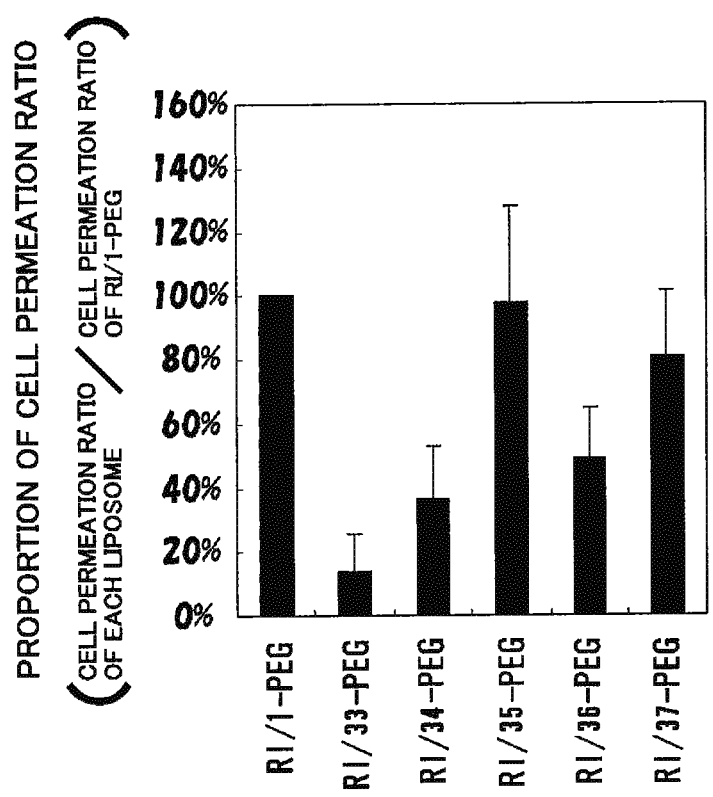

FIG. 13 is a graph showing the proportions of the cell, permeation ratios of RI/33-PEG, RI/34-PEG, RI/35-PEG, RI/36-PEG, and RI/37-PEG, assuming a cell permeation ratio of RI/1-PEG of 100(%).

Figure 14:
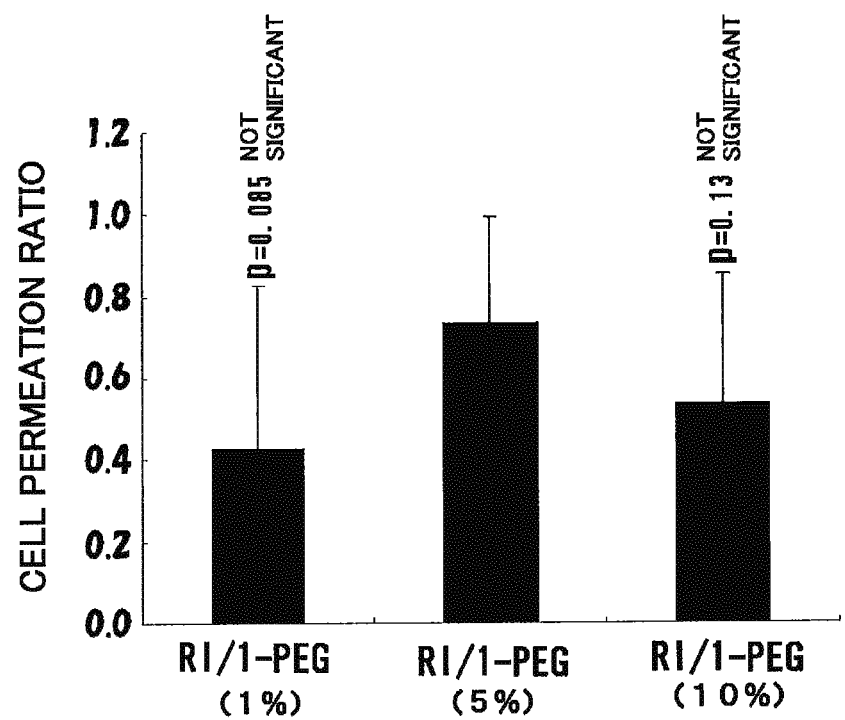

FIG. 14 is a graph showing the cell permeation ratio of RI/1-PEG when the percentage of a modified lipid 1 was 1%, 5%, or 10%.

Figure 15:
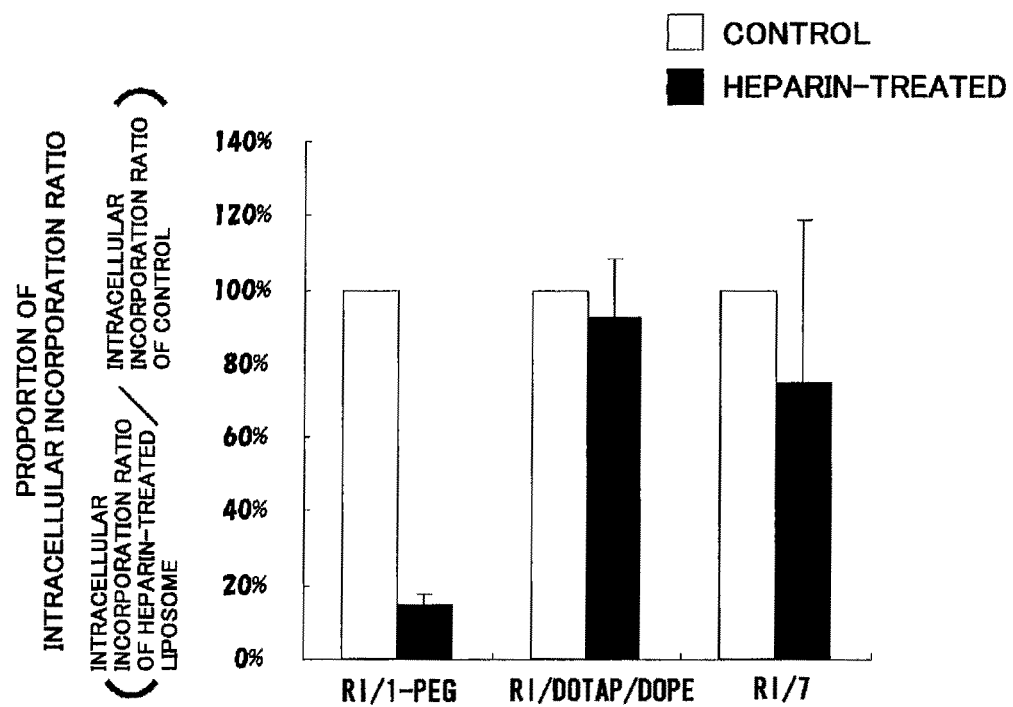

FIG. 15 is a graph showing the proportion of the cell permeation ratio of each of heparin-treated RI/1-PEG, RI/DOTAP/DOPE, and RI/7, assuming a cell permeation ratio of each of heparin-untreated RI/1-PEG, RI/DOTAP/DOPE, and RI/7 of 100(%).

Figure 16:
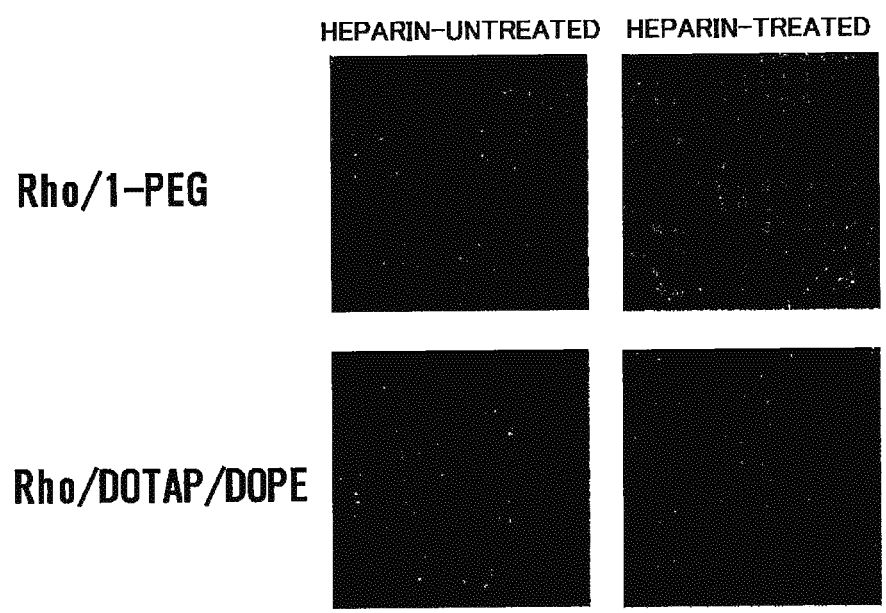

FIG. 16 is a series of photographs showing the results of fluorescent observation of the states of intracellular incorporation of heparin-treated Rho/1-PEG and Rho/DOTAP/DOPE and heparin-untreated Rho/1-PEG and Rho/DOTAP/DOPE.

Figure 17:
Figure 17:

FIG. 17 is a pair of photographs showing the results of fluorescent observation of the intracellular localization of Rho/1-PEG, early endosomes, late endosomes, and lysosomes in MBEC4 cells.

Figure 18:
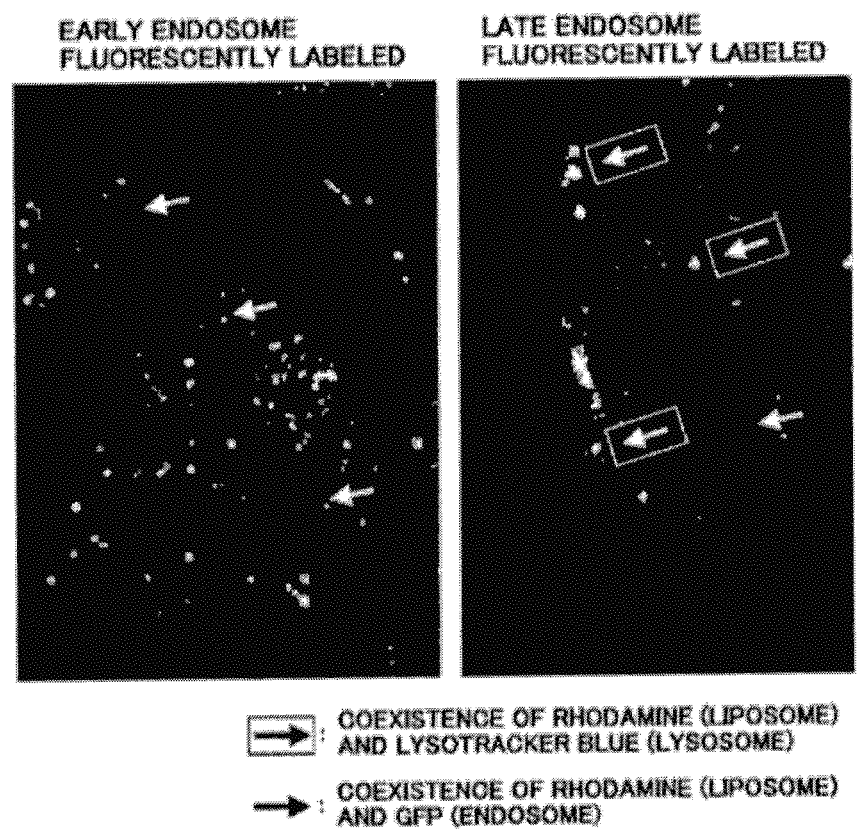

FIG. 18 is a pairs of photographs showing the results of fluorescent observation of the intracellular localization of Rho/1-PEG, early endosomes, late endosomes, and lysosomes in CHO-K1 cells.

DESCRIPTION OF THE INVENTION

The peptides imparting cell permeability to a lipid membrane structure and/or enhancing the cell permeability of a lipid membrane structure according to the present invention, and the lipid membrane structure comprising, as a constituent lipid, a lipid bound to such a peptide and having cell permeability or showing enhanced cell permeability will be described below in detail.

The peptides imparting cell permeability to a lipid membrane structure and/or enhancing the cell permeability of a lipid membrane structure according to the present invention impart the function of being capable of permeating cells (cell permeability) to a lipid membrane structure typified by a liposome or enhance the cell permeability of the lipid membrane structure typified by a liposome. In other words, the peptides imparting cell permeability to a lipid membrane structure and/or enhancing the cell permeability of a lipid membrane structure according to the present invention impart cell permeability to, or impart and enhance the cell permeability of, a lipid membrane structure not having cell permeability or enhance the cell permeability of a lipid membrane structure having cell permeability.

Here, for the purpose of the present invention, "cell permeation" refers to that a substance incorporated into a cell from a particular region of the cell membrane is released from a different particular region of the cell membrane to the outside of the cell; representative examples thereof can include transcytosis. The transcytosis takes place mainly in epithelial cells such as vascular endothelial cells and fetal small intestinal epithelial cells; in vascular endothelial cells, for example, a particular substance such as albumin bound to an extracellular receptor is incorporated from the intravascular lumen (the side of blood) by endocytosis and then released to the extravascular lumen (perivascular tissue) by exocytosis. In fetal small intestinal epithelial cells, IgG of maternal origin is incorporated from the blood of the mother body by endocytosis and then released into the fetal blood by exocytosis.

The peptides imparting cell permeability to a lipid membrane structure and/or enhancing the cell permeability of a lipid membrane structure according to the present invention each have an amino acid sequence of $LX_1X_2X_1X_1X_1L$, $LLX_2X_1X_1X_1L$, or $LX_1X_2X_1X_1L$, wherein L represents a leucine residue; $X_1$ represents a polar amino acid residue; and $X_2$ represents a polar, non-charged and branched chain amino acid residue.

In the amino acid sequence $LX_1X_2X_1X_1X_1L$, $LLX_2X_1X_1X_1L$, or $LX_1X_2X_1X_1L$ of each of the peptides imparting cell permeability to a lipid membrane structure and/or enhancing the cell permeability of a lipid membrane structure according to the present invention, $X_1$ represents a polar amino acid residue. The polar amino acid may be any of glycine (G), asparagine (N), cysteine (C), glutamine (Q), serine (S), threonine (T), tyrosine (Y), aspartic acid (D), glutamic acid (E), arginine (R), histidine (H), and lysine (K); however, preferred are arginine (R), lysine (K), serine (S), and aspartic acid (D). The 4 amino acid residues or 3 amino acid residues represented by $X_1$ may be different 2 to 4 or 2 or 3 types of amino acid residues selected from the above group, or may be the same amino acid residue.

In the amino acid sequence $LX_1X_2X_1X_1X_1L$, $LLX_2X_1X_1X_1L$, or $LX_1X_2X_1X_1L$ of each of the peptides imparting cell permeability to a lipid membrane structure and/or enhancing the cell permeability of a lipid membrane structure according to the present invention, $X_2$ represents a polar, non-charged and branched chain amino acid residue. The polar, non-charged and branched chain amino acid may be any of glycine (G), asparagine (N), cysteine (C), glutamine (Q), serine (S), threonine (T), and tyrosine (Y); however, preferred is glutamine (Q).

The amino acid sequence of each of the peptides imparting cell permeability to a lipid membrane structure and/or enhancing the cell permeability of a lipid membrane structure according to the present invention is preferably LRQRRRL (SEQ ID NO: 1), LLQRRRL (SEQ ID NO: 14), LRQRRL (SEQ ID NO: 26), LKQKKKL (SEQ ID NO: 15), LLQKKKL (SEQ ID NO: 38), LKQKKL (SEQ ID NO: 39), LRQSSSL (SEQ ID NO: 35), LLQSSSL (SEQ ID NO: 40), LRQSSL (SEQ ID NO: 41), LRQRDDL (SEQ ID NO: 37), LLQRDDL (SEQ ID NO: 42), or LRQRDL (SEQ ID NO: 43), wherein L represents a leucine residue; R represents an arginine residue; Q represents a glutamine residue; K represents a lysine residue; S represents a serine residue; and D represents an aspartic acid residue.

The peptides imparting cell permeability to a lipid membrane structure and/or enhancing the cell permeability of a lipid membrane structure according to the present invention each comprise an amino acid sequence of $LX_1X_2X_1X_1X_1L$, $LLX_2X_1X_1X_1L$, or $LX_1X_2X_1X_1L$, wherein L represents a leucine residue; $X_1$ represents a polar amino acid residue; and $X_2$ represents a polar, non-charged and branched chain amino acid residue; however, the peptides imparting cell permeability to a lipid membrane structure and/or enhancing the cell permeability of a lipid membrane structure according to the present invention include peptides comprising amino acid sequences in each of which one or a plurality of conservative amino acid substitutions are contained in the above amino acid sequence provided that they have the function of imparting cell permeability to the lipid membrane structure, enhancing the cell permeability of the lipid membrane structure, or imparting cell permeability to the lipid membrane structure as well as enhancing the cell permeability thereof.

For the purpose of the present invention, the conservative amino acid substitution is substitution observed in the range in which it can generally be performed without changing the physiological activity of the resulting molecule, i.e., in the range of conservative substitution (Watson et al., Molecular Biology of Gene and the like); examples thereof can include substitution occurring between amino acids having similar branched chains (members of an amino acid family), such as: the acidic amino acids of aspartic acid and glutamic acid; the basic amino acids of lysine, arginine, and histidine; the non-polar amino acids of alanine, valine, leucine, isoleucine, proline, phenylalanine, methionine, and tryptophan; the polar, non-charged and branched chain amino acids of glycine, asparagine, cysteine, glutamine, serine, threonine, and tyrosine; and the aromatic amino acids of phenylalanine, tryptophan, and tyrosine. Similarly, classification can be as: the acidic amino acids of aspartic acid and glutamic acid; the basic amino acids of lysine, arginine, and histidine; the aliphatic amino acids of glycine, alanine, valine, leucine, isoleucine, serine, and threonine (which can also be classified as the aliphatic hydroxyamino acids of serine and threonine); the aromatic amino acids of phenylalanine, tyrosine, and tryptophan; amides of asparagine and glutamine; and the sulfur-containing amino acids of cysteine and methionine.

The peptides imparting cell permeability to a lipid membrane structure and/or enhancing the cell permeability of a lipid membrane structure according to the present invention include those peptides in which the deletion, substitution (excluding the above conservative amino acid substitution), insertion and/or addition of one or several amino acids is made provided that they have the function of imparting cell permeability to the lipid membrane structure, enhancing the cell permeability of the lipid membrane structure, or imparting cell permeability to the lipid membrane structure as well as enhancing the cell permeability thereof. The specific deletion range is typically 1 to 3, preferably 1 to 2, more preferably 1 amino acid; the specific range of substitution excluding the above conservative amino acid substitution is typically 1 to 3, preferably 1 to 2, more preferably 1 amino acid; the specific insertion range is typically 1 to 5, preferably 1 to 3, more preferably 1 to 2, still more preferably 1 amino acid; and the specific addition range is typically 1 to 5, preferably 1 to 3, more preferably 1 to 2, still more preferably 1 amino acid.

For example, as will hereinafter be described, when each of the peptides imparting cell permeability to a lipid membrane structure and/or enhancing the cell permeability of a lipid membrane structure according to the present invention is bound to a lipid membrane structure, it may be subjected to the addition of one or several amino acids to bind to the lipid membrane structure while maintaining the function of imparting cell permeability to the lipid membrane structure, the function of enhancing the cell permeability of the lipid membrane structure, or the function of imparting cell permeability to the lipid membrane structure as well as enhancing the cell permeability thereof, for example, by adding a tyrosine residue and a cysteine residue C-terminal to an amino acid sequence of $LX_1X_2X_1X_1X_1L$, $LLX_2X_1X_1X_1L$, or $LX_1X_2X_1X_1L$, wherein L represents a leucine residue; $X_1$ represents a polar amino acid residue; and $X_2$ represents a polar, non-charged and branched chain amino acid residue; such resultant peptides are also embraced in the present invention.

The peptides imparting cell permeability to a lipid membrane structure and/or enhancing the cell permeability of a lipid membrane structure according to the present invention can be synthesized using a method properly selectable by those skilled in the art on the basis of the sequences thereof. Examples of the method can include a method involving preparing a recombinant vector containing DNA encoding a peptide according to the present invention, introducing the prepared vector into suitable host cells, culturing the resultant transformant in a medium, and collecting the peptide from the culture, and a method involving expressing DNA encoding a peptide according to the present invention in a cell-free protein synthesis system, in addition to a peptide synthesis method involving chemically polymerizing amino acids one after another. In this respect, each of the synthesis methods may use any method including a common method widely known to those skilled in the art.

The peptides imparting cell permeability to a lipid membrane structure and/or enhancing the cell permeability of a lipid membrane structure according to the present invention impart cell permeability, particularly in epithelial cells, to the lipid membrane structure, enhance the epithelial cell permeability of the lipid membrane structure, or impart epithelial cell permeability to the lipid membrane structure as well as enhancing the epithelial cell permeability thereof. Here, the epithelial cells are cells forming the epithelium by assuming a two-dimensional layer structure on the tissue surface, and have the function of selectively passing a substance through the cells by transcytosis and the like in addition to forming the tight junction between the cells to suppress the passage of a substance due to diffusion or penetration. Examples of the epithelial cells can include lymphatic endothelial cells, serous mesothelial cells, urothelial cells, pelvic epithelial cells, respiratory tract epithelial cells, tracheal epithelial cells, bronchial epithelial cells, intestinal epithelial cells, epidermal cells, nasal epithelial cells, and pharyngeal epithelial cells in addition to the above-described vascular endothelial cells and fetal small intestinal epithelial cells. In the present Examples, vascular endothelial cells are used as preferable epithelial cells.

The lipid membrane structure having cell permeability imparted and/or enhanced by the binding of a peptide imparting cell permeability to a lipid membrane structure and/or enhancing the cell permeability of a lipid membrane structure according to the present invention transfers to lysosomes for decomposition in cells not permeated by the structure. Specifically, the lipid membrane structure having cell permeability imparted and/or enhanced by the binding of a peptide imparting cell permeability to a lipid membrane structure and/or enhancing the cell permeability of a lipid membrane structure according to the present invention is administered into the blood by encapsulating a substance such as an agent, a protein, or a nucleic acid therein to pass the lipid membrane structure through vascular endothelial cells to cause it to reach cells at a target site, then releases the encapsulated substance in the cells at the target site, and thereby can properly exert a function as a drug delivery vector.

The lipid membrane structure having cell permeability imparted and/or enhanced by the binding of a peptide of the present invention is incorporated into cells mainly via heparan sulfate proteoglycan present in lipid raft for cell permeation. The lipid raft is one of microdomains on the cell membrane, and is an area about 100 nm in diameter in which molecules such as sphingolipid, glycolipid, cholesterol, receptor protein, or glycoprotein (e.g., heparan sulfate proteoglycan) assemble. The lipid raft functions as a window for signal transduction or substance transport through the actions of these assembling characteristic molecules.

The lipid membrane structure having cell permeability or showing enhanced cell permeability according to the present invention comprises, as a constituent lipid, the above-described lipid bound to a peptide of the present invention. Methods for identifying the cell permeability of the lipid membrane structure can include, for example, a method which involves causing cells to form the tight junction therebetween, adding the lipid membrane structure to the resultant, and calculating the permeation rate thereof. For example, when a device for evaluating cell permeability (Japanese Patent Application No. 2009-275877) is used, the permeation rate for a case where cells are not cultured (the cell-free permeation rate of liposomes) and the permeation rate for a case where cells forming the tight junction are cultured (the cell-laden permeation rate of liposomes) can be calculated to determine the ratio therebetween (cell permeation ratio) to identify the cell permeability of the lipid membrane structure.

According to the present invention, a preferred form of the lipid membrane structure is a closed vesicle having a lipid hilayr membrane structure; examples of such a lipid membrane structure can include single compartment liposomes such as SUV (a small unilamella vesicle), LUV (a large unilamella vesicle), and GUV (a giant unilamella vesicle). According to the present invention, the size of the lipid membrane structure is not particularly limited; however, it is preferably 50 nm to 800 nm in diameter, more preferably 80 to 150 nm in diameter.

The type of the lipid constituting the lipid membrane structure according to the present invention is not particularly limited; however, preferred is a phospholipid, a glycolipid, a sterol, a long-chain aliphatic alcohol, or a glycerin fatty acid ester, and it also does not matter whether the type is a cationic lipid, a neutral lipid, or an anionic lipid.

Examples of the phospholipid can include phosphatidylcholines (for example, dioleoyl phosphatidylcholine, dilauroyl phosphatidylcholine, dimyristoyl phosphatidylcholine, dipalmitoyl phosphatidylcholine, and distearoyl phosphatidylcholine), phosphatidylglycerols (for example, dioleoyl phosphatidylglycerol, dilauroyl phosphatidylglycerol, dimyristoyl phosphatidylglycerol, dipalmitoyl phosphatidylglycerol, and distearoyl phosphatidylglycerol), phosphatidylethanolamines (for example, dioleoyl phosphatidylethanolamine, dilauroyl phosphatidylethanolamine, dimyristoyl phosphatidylethanolamine, dipalmitoyl phosphatidylethanolamine, distearoyl phosphatidylethanolamine (DSPE), and dioleoylglycerophosphoethanolamine (DOPE)), phosphatidylserine, phosphatydylinositol, phosphatidic acid, cardiolipin, and hydrogenated products thereof, and natural lipids derived from egg yolk, soybean, and other animals and plants (for example, egg yolk lecithin and soybean lecithin); these may be used alone or in a mixture of 2 or more thereof. The phospholipid is used as the major constituent of the lipid membrane structure. The usage amount thereof is preferably 10 to 100% (molar ratio), more preferably 50 to 80% (molar ratio), based on the total lipid of the lipid membrane structure; however, it is not particularly limited to these values.

Examples of the glycolipid can include sphingomyelin, glyceroglycolipids such as sulfoxyribosyl glyceride, diglycosyl diglyceride, digalactosyl diglyceride, galactosyl diglyceride, and glycosyl diglyceride, and glycosphingolipids such as galactosyl cerebroside, lactosyl cerebroside, and ganglioside; these can be used alone or in a mixture of 2 or more thereof.

Examples of the sterol can include animal-derived sterols such as cholesterol, cholesterol succinate, lanosterol, dihydrolanosterol, desmosterol, and dihydrocholesterol, plant-derived sterols (phytosterols) such as stigmasterol, sitosterol, campesterol, and brassicasterol, and microorganism-derived sterols such as zymosterol and ergosterol; these can be used alone or in a mixture of 2 or more thereof. These sterols can be generally used to physically or chemically stabilize a lipid bilayer or to regulate the fluidity of the membrane. The usage amount thereof is preferably 5 to 40% (molar ratio), more preferably 10 to 30% (molar ratio), based on the total lipid of the lipid membrane structure, based on the total lipid of the lipid membrane structure; however, it is not particularly limited to these values.

Examples of the long-chain fatty acid or the long-chain aliphatic alcohol can use a fatty acid having 10 to 20 carbons or its alcohol. Examples of the long-chain fatty acid or the long-chain aliphatic alcohol can include saturated fatty acids such as palmitic acid, stearic acid, lauric acid, myristic acid, pentadecyl acid, arachidic acid, margaric acid, and tuberculostearic acid, unsaturated fatty acids such as palmitoleic acid, oleic acid, arachidonic acid, vaccenic acid, linoleic acid, linolenic acid, arachidonic acid, and eleostearic acid, oleyl alcohol, stearyl alcohol, lauryl alcohol, myristyl alcohol, cetyl alcohol, and linolyl alcohol; these can be used alone or in a mixture of 2 or more thereof. The usage amount is preferably 5 to 40% (molar ratio), more preferably 10 to 30% (molar ratio), based on the total lipid of the lipid membrane structure, based on the total lipid of the lipid membrane structure; however, it is not particularly limited to these values.

Examples of the glycerin fatty acid ester can include a monoacylglyceride, a diacylglyceride, and a triacylglyceride; these can be used alone or in a mixture of 2 or more thereof. The usage amount thereof is preferably 5 to 40% (molar ratio), more preferably 10 to 30% (molar ratio), based on the total lipid of the lipid membrane structure, based on the total lipid of the lipid membrane structure; however, it is not particularly limited to these values.

Examples of the cationic lipid can include, in addition to the above-described lipids, dioctadecyldimethylammonium chloride (DODAC), N-(2,3-dioleyloxy)propyl-N,N,N-trimethylammonium (DOTMA), didodecylammonium bromide (DDAB), 1,2-dioleoyloxy-3-trimethylammonio-propane (DOTAP), 3β-N—(N',N',-dimethyl-aminoethane)-carbamol cholesterol, (DC-Chol), 1,2-dimyristoyloxypropyl-3-dimethylhydroxyethyl ammonium (DMRIE), and 2,3-dioleyloxy-N-[2(sperminecarboxamido)ethyl]-N,N-dimethyl-1-propanaminum trifluoroacetate (DOSPA); these can be used alone or in a mixture of 2 or more thereof. Because the cationic lipid has cytotoxicity, it is preferable to minimize the amount of the cationic lipid contained in the lipid bilayer in terms of reducing the cytotoxicity of the liposome of the present invention; the percentage of the cationic lipid in the total lipid constituting the lipid bilayer is preferably 0 to 40% (molar ratio), more preferably 0 to 20% (molar ratio).

Examples of the neutral lipid can include, in addition to the above-described lipids, a diacylphosphatidylcholine, a diacylphosphatidylethanolamine, and ceramide; these can be used alone or in a mixture of 2 or more thereof. Examples of the anionic lipid can include, in addition to the above-described lipids, a diacylphosphatidylserine, a diacylphosphatidic acid, N-succinylphosphatidylethanolamine (N-succinylPE), and phosphatidyl ethylene glycol; these can be used alone or in a mixture of 2 or more thereof.

The lipid membrane constituting the lipid membrane structure having cell permeability or showing enhanced cell permeability according to the present invention may comprise a plurality of lipids bound to a peptide of the present invention. The plurality of such lipids may be optionally selected, for example, from: a phospholipid bound to a peptide of the present invention and another phospholipid bound to a peptide of the present invention; a phospholipid bound to a peptide of the present invention and a sterol bound to a peptide of the present invention; a phospholipid bound to a peptide of the present invention and a glycolipid bound to a peptide of the present invention.

According to the present invention, the lipid membrane of the lipid membrane structure may contain, in addition to the above-described lipid(s), an antioxidant such as tocopherol, propyl gallate, ascorbyl palmitate, or butylated hydroxytoluene, a positive charge-imparting substance such as stearylamine or oleylamine, a negative charge-imparting substance such as dicetyl phosphate, and a membrane protein such as a membrane extrinsic protein or an integral membrane protein; the content thereof may be regulated as needed.

A preferred aspect of the lipid membrane structure having cell permeability or showing enhanced cell permeability according to the present invention is a lipid membrane structure comprising, as a constituent lipid, a lipid bound to a peptide, in which a tyrosine residue, a cysteine residue, a hydrophilic polymer, and the lipid are bound in that order to the C-terminal end of a peptide according to the present invention. Specifically, it is a lipid membrane structure having a structure in which a peptide according to the present invention is bound to a part of a maleimidized hydrophilic polymer via a cysteine residue added C-terminal thereto, the hydrophilic polymer being further bound to a constituent of the liposome, particularly a lipid.

For the purpose of the present invention, the term "lipid bound to a peptide" includes not only a lipid directly bound to a peptide but also a lipid bound to a peptide via some linker such as a different amino acid residue or a hydrophilic polymer. According to the present invention, preferred examples of the linker can include a high-molecular compound or hydrophilic polymer in which a tyrosine residue, a cysteine residue, and a hydrophilic polymer are bound in that order.

A hydrophilic polymer and a peptide according to the present invention can be bound by forming the covalent bonding between a functional group of the hydrophilic polymer and a functional group of the peptide according to the present invention. Typical examples of the combination of functional groups capable of forming covalent bonding can include an amino group/a carboxyl group, an amino group/an acyl halide group, an amino group/an N-hydroxysuccinimide ester group, an amino group/a benzotriazole carbonate group, an amino group/an aldehyde group, a thiol group/a maleimide group, and a thiol group/a vinylsulfone group; however, because the peptide according to the present invention is a peptide containing 3 or more polar amino acid residues (including a polar, non-charged and branched chain amino acid residue), it is preferable to newly add an amino acid residue having a thiol group to the peptide according to the present invention and bind to a hydrophilic polymer using the thiol group.

Lu et al. (J. Controlled release, 2006, 110: 505-513) have reported a method for binding a thiol group-containing peptide or a peptide to which an amino acid residue with a thiol group such as cysteine is added, to a hydrophilic polymer via the thiol group, and the binding of the resultant hydrophilic polymer to a lipid. The liposome of the present invention can be prepared using, but not limiting to, the method of Lu et al. The amino acid residue with a thiol group may be added N-terminal or C-terminal to a peptide according to the present invention. The amino acid residue with a thiol group may be inserted into a part other than the N-terminal end or C-terminal end of a peptide according to the present invention.

Lipid generally has chemically activatable functional groups such as a carbonyl group, an amino group, and a hydroxyl group; thus, in addition to the above-described preparation method, a lipid bound to a peptide according to the present invention can be prepared by the chemical reaction between any of these suitable functional groups and a functional group of a peptide according to the present invention, a functional group of an amino acid added to a peptide according to the present invention, or a functional group of a hydrophilic polymer bound to the peptide. For example, when the lipid is phosphatidylethanolamine (PE) and a peptide according to the present invention is bound thereto via the above high-molecular compound, a method of Martin et al. (Biochem. Biophys. Acta, 1992, 1113: 171-199) is known. Specifically, the PE bound to a peptide according to the present invention can be prepared by converting the hydroxyl group of a hydrophilic polymer bound to the peptide to a carboxylic acid and performing the condensation reaction between the carboxyl group and the amino group of PE.

A method reported by Bhattacharya et al. (Langmuir, 2001, 17: 2067-2075) is known as a method for preparing a sterol bound to a peptide according to the present invention via the above high-molecular compound. Specifically, the sterol bound to a peptide according to the present invention can be prepared by activating the hydroxyl group of a sterol with a tosyl group and using, in an organic solvent, an SN2 reaction by the hydroxyl group of a hydrophilic polymer bound to the peptide.

In addition, a method for preparing a long-chain fatty acid bound to a peptide according to the present invention via the high-molecular compound can be carried out by introducing an amino group into a hydrophilic polymer bound to the peptide and performing the condensation reaction between the amino group and the carboxyl group of a long-chain fatty acid.

The hydrophilic polymer usable in the present invention is not particularly limited provided that it can constitute the above-described high-molecular compound, enables the binding of a peptide according to the present invention to a lipid via the high-molecular compound, and can constitute the lipid membrane structure having cell permeability or showing enhanced cell permeability. Examples of the hydrophilic polymer can include polymers having hydrophilic groups such as a hydroxy group, a carboxyl group, a carboxylate group, a hydroxyethyl group, a polyoxyethyl group, a hydroxypropyl group, a polyoxypropyl group, an amino group, an aminoethyl group, an aminopropyl group, an ammonium group, an amide group, a carboxymethyl group, a sulfonic acid group, and a phosphoric acid group; specific examples thereof can include gum arabic, casein, gelatin, starch derivatives, carboxymethylcellulose and its salts, cellulose acetate, sodium alginate, vinyl acetate-maleic acid copolymers, styrene-maleic acid copolymers, polyacrylic acids and salts thereof, polymethacrylic acids and salts thereof, a homopolymer and copolymers of hydroxyethyl methacrylate, a homopolymer and copolymers of hydroxyethyl acrylate, a homopolymer and copolymers of hydroxypropyl methacrylate, a homopolymer and copolymers of hydroxypropyl acrylate, a homopolymer and copolymers of hydroxybutyl methacrylate, a homopolymer and copolymers of hydroxybutyl acrylate, polyethylene glycols, hydroxypropylene polymers, polyvinyl alcohols, hydrolyzed polyvinyl acetate having a hydrolysis degree of 60 mol % or more, preferably 80 mol % or more, polyvinyl formal, polyvinyl butyral, polyvinylpyrrolidone, a homopolymer and copolymers of acrylamide, a homopolymer and copolymers of methacrylamide, a homopolymer and copolymers of N-methylolacrylamide, alcohol-soluble nylon, and a polyether of 2,2-bis-(4-hydroxyphenyl)-propane and epichlorohydrin; however, polyethylene glycol is preferable.

The percentage P of a lipid bound to a peptide according to the present invention in the lipid membrane structure having cell permeability or showing enhanced cell permeability according to the present invention is 1 mol %≤P≤10 mol %, assuming a total amount of lipids constituting the lipid membrane of 100(%).

According to the present invention, the lipid membrane structure can be prepared using a known method such as, for example, a hydration method, a sonic disintegration method, an ethanol infusion method, an ether infusion method, a reverse phase evaporation method, a surfactant method, or a freezing and thawing method. In the case of the hydration method, for example, a lipid membrane structure comprising, as a constituent of the membrane, a lipid bound to a peptide according to the present invention can be produced by dissolving the lipid bound to a peptide according to the present invention and further a different lipid and any component contained in the lipid membrane described hereinabove in an organic solvent, evaporatively removing the organic solvent to provide a lipid membrane, and hydrating and stirring or sonicating the lipid membrane.

The lipid membrane structure having cell permeability or showing enhanced cell permeability according to the present invention can also be obtained by dissolving the above-described lipid or a different lipid in an organic solvent, evaporatively removing the organic solvent to provide a lipid membrane, hydrating and stirring or sonicating the lipid membrane to produce liposomes, and adding a peptide according to the present invention to the external solution of the liposomes to introduce the peptide into the surface of the liposomes.

In the above method, the organic solvent may use, for example, a hydrocarbon such as pentane, hexane, heptane, or cyclohexane, a halogenated hydrocarbon such as methylene chloride or chloroform, an aromatic hydrocarbon such as benzene or toluene, a lower alcohol such as methanol or ethanol, an ester such as methyl acetate or ethyl acetate, or a ketone such as acetone, alone or in a combination of 2 or more thereof.

Passage through a filter having a predetermined pore size can provide the lipid membrane structure having a constant particle size distribution.

Various physiologically active substances such as an agent, a nucleic acid, a peptide, a protein, a saccharide, and a complex thereof can each be encapsulated in the lipid membrane structure of the present invention, and can be properly selected according to the object of diagnosis, treatment, or the like. When the physiologically active substance is water-soluble, the substance can be added to an aqueous solvent used for hydrating a lipid membrane in producing the lipid membrane structure to encapsulate the physiologically active substance in the aqueous phase in the interior of the lipid membrane structure. When the physiologically active substance is lipid-soluble, the substance can be added to an organic solvent used in producing the lipid membrane structure to encapsulate the physiologically active substance in the membrane of the lipid membrane structure.

According to the present invention, the lipid membrane structure can be used by dispersing it in a suitable aqueous solvent such as saline, phosphate buffer, citrate buffer, or acetate buffer. Additives such as a saccharide, a polyhydric alcohol, a water-soluble polymer, a non-ionic surfactant, an antioxidant, a pH regulator, and a hydration promoter may be added to the dispersion, as needed. According to the present invention, the lipid membrane structure may also be preserved in a state of the dispersion being dried. In addition, according to the present invention, the lipid membrane structure can be orally administered as well as can be parenterally administered into the vein, the abdominal cavity, the subcutis, the nose, or the like.

Then, the present invention provides an agent imparting cell permeability to, and/or enhancing the cell permeability of, a lipid membrane structure. The agent imparting cell permeability to, and/or enhancing the cell permeability of, a lipid membrane structure according to the present invention comprises, as an active ingredient, a peptide having an amino acid sequence of $LX_1X_2X_1X_1X_1L$, $LLX_2X_1X_1X_1L$, or $LX_1X_2X_1X_1L$, wherein L represents a leucine residue; $X_1$ represents a polar amino acid residue; and $X_2$ represents a polar, non-charged and branched chain amino acid residue. In other words, the agent imparting cell permeability to, and/or enhancing the cell permeability of, a lipid membrane structure according to the present invention comprises, as an active ingredient, the peptide imparting cell permeability to the lipid membrane structure according to the present invention and/or enhancing the cell permeability of the lipid membrane structure.

The present invention provides a method for producing a lipid membrane structure having cell permeability or showing enhanced cell permeability. The method for producing a lipid membrane structure having cell permeability or showing enhanced cell permeability according to the present invention comprises the step of:

(a) modifying a lipid membrane structure with a peptide having an amino acid sequence of the following: $LX_1X_2X_1X_1X_1L$, $LLX_2X_1X_1X_1L$, or $LX_1X_2X_1X_1L$, wherein L represents a leucine residue; $X_1$ represents a polar amino acid residue; and $X_2$ represents a polar, non-charged and branched chain amino acid residue.

In the step (a), the peptide having an amino acid sequence of the following: $LX_1X_2X_1X_1X_1L$, $LLX_2X_1X_1X_1L$, or $LX_1X_2X_1X_1L$, wherein L represents a leucine residue; $X_1$ represents a polar amino acid residue; and $X_2$ represents a polar, non-charged and branched chain amino acid residue, may use the same as the peptide imparting cell permeability to the lipid membrane structure according to the present invention and/or enhancing the cell permeability of the lipid membrane structure. In addition, in the step (a), the lipid membrane structure may use the same as the lipid membrane structure used for the lipid membrane structure having cell permeability or showing enhanced cell permeability according to the present invention.

In the step (a), the method for modifying a lipid membrane structure with a peptide is not particularly limited, and may be performed using a method properly selectable by those skilled in the art. Examples of such a method can include a method involving first binding a peptide to a lipid molecule and then preparing a lipid membrane structure comprising the peptide-bound lipid molecule as a constituent lipid, in addition to a method involving preparing a lipid membrane structure and then adding a peptide to bind the peptide to the constitutive lipid of the lipid membrane structure. In addition, the peptide may be bound to the constituent lipid of the lipid membrane structure directly or via the above-described linker. The method for binding a peptide to a lipid molecule, the method for preparing a lipid membrane structure, and the method for adding the peptide to the lipid membrane to bind the peptide to the constituent lipid of the lipid membrane structure are as described above.

Examples of the mode of the binding between the peptide and the lipid membrane structure can include non-covalent bonding such as hydrogen bonding, ionic bonding, hydrophobic bonding, or van der Waals binding, and covalent bonding such as disulfide bonding or peptide bonding.

The peptides imparting cell permeability to and/or enhancing the cell permeability of a lipid membrane structure according to the present invention and the lipid membrane structure comprising, as a constituent lipid, a lipid bound to such a peptide and having cell permeability or showing enhanced cell permeability will be described below with reference to Examples. However, the technical scope of the present invention is not intended to be limited to the features exhibited by these Examples.

EXAMPLES

Example 1

Preparation of Experimental Material (1) Preparation of Krebs Buffer

Krebs buffer (pH 7.3) having the following composition was prepared using sterilized water as a solvent.

| Composition of Krebs Buffer | |
|---|---|
| KCl (Wako Pure Chemical Industries Ltd.) | 4.8 mmol/L |
| KH$_2$PO$_4$ (Wako Pure Chemical Industries Ltd.) | 1.0 mmol/L |
| MgSO$_4$ (Wako Pure Chemical Industries Ltd.) | 1.2 mmol/L |
| 2-[4-(2-Hydroxyethyl)-1-piperazinyl]ethanesulfonic acid (HEPES) (Wako Pure Chemical Industries Ltd.) | 12.5 mmol/L |
| CaCl$_2$ (Wako Pure Chemical Industries Ltd.) | 1.5 mmol/L |
| NaCl (Nacalai Tesque Inc.) | 120.0 mmol/L |
| NaHCO$_3$ (Wako Pure Chemical Industries Ltd.) | 23.8 mmol/L |
| Glucose (Wako Pure Chemical Industries Ltd.) | 5.0 mmol/L |

(2) Selection of Peptide by In Vivo Phage Display

According to a method as described in Japanese Patent Laid-Open No. 2008-31142, in vivo phage display was performed to select the following peptides as candidates of the peptides imparting cell permeability or enhancing cell permeability from among the resultant peptides accumulating in muscle tissue.

```
Peptide 1;    LRQRRRL    (SEQ ID NO: 1)
Peptide 2;    RKRIRMR    (SEQ ID NO: 2)
Peptide 3;    RRRRQNI    (SEQ ID NO: 3)
Peptide 4;    RKRSRMR    (SEQ ID NO: 4)
Peptide 5;    IRQRRRR    (SEQ ID NO: 5)
``` wherein the end on the left facing represents an N-terminal; the end on the right facing represents a C-terminal; L represents a leucine residue; R represents an arginine residue; Q represents a glutamine residue; K represents a lysine residue; I represents an isoleucine residue; M represents a methionine residue; N represents an asparagine residue; and S is a serine residue (hereinafter the same shall apply).

(3) Preparation of Peptide-PEG Modified Lipid

Peptides consisting of amino acid sequences having tyrosine (Y) and cysteine (C) added to the C-terminal ends of the peptides selected in (1) of this Example and R8 (RRRRRRRR: SEQ ID NO: 6) (Kentaro Kogure, Yakugaku Zasshi, 127 (10): 1685-1691, 2007) as a peptide known to impart certain intracellular migration ability to liposomes were prepared by chemical synthesis under commission to Hokkaido System Science Co., Ltd. Each of these peptides and Mal-PEG2000-DSPE (product name: DSPE-020MA, NOF Corporation) as a conjugate between a polyethylene glycol of a molecular weight of 2,000 having a maleimide group added (hereinafter, sometimes simply referred to as "PEG") and L-α-distearoyl phosphatidyl ethanolamine (DSPE) were dissolved in pure water to concentrations of 2 mmol/L each and incubated at room temperature for 24 hours while stirring with a stirrer to prepare each of the following peptide-PEG modified lipids.

```
Modified lipid 1;
LRQRRRL (SEQ ID NO: 1)-YC-PEG-DSPE

Modified lipid 2;
RKRIRMR (SEQ ID NO: 2)-YC-PEG-DSPE

Modified lipid 3;
RRRRQNI (SEQ ID NO: 3)-YC-PEG-DSPE
```

-continued

```
Modified lipid 4;
RKRSRMR (SEQ ID NO: 4)-YC-PEG-DSPE

Modified lipid 5;
IRQRRRR (SEQ ID NO: 5)-YC-PEG-DSPE

Modified lipid 6;
RRRRRRRR(SEQ ID NO: 6)-YC-PEG-DSPE
``` wherein Y represents a tyrosine residue and C represents a cysteine residue (hereinafter the same shall apply).

(4) Preparation of Liposome

[4-1] Preparation of RI-Labeled Peptide-PEG Modified Liposome

Egg-yolk phosphatidylcholine {L-α-Phosphatidylcholine, Egg (Powder); Avanti Polar Lipids} and cholesterol {Cholesterol (Powder); Avanti Polar Lipids} were mixed to (egg-yolk phosphatidylcholine):(cholesterol)=7:3 to prepare a mixed lipid powder. Subsequently, the prepared mixed lipid powder was dissolved in ethanol to 1 nmol/μL to prepare a mixed lipid ethanol solution. The mixed lipid ethanol solution and an aqueous solution of each of the modified lipids prepared in (3) of this Example were injected into a glass test tube to a mol % ratio of (the mixed lipid):(each modified lipid prepared in (3) of this Example) of 95:5 and a total solution volume of 137.5 μL. Thereto were added 2,500,000 dpm to 5,000,000 dpm of $^3$H-cholesteryl hexadecyl ether (CHE) as a radioactive isotope (RI) and 112.5 μL, of chloroform, which was subjected to vortex treatment for short time, followed by removing the ethanol solvent using a stream of nitrogen gas according to an ordinary method. Subsequently, the lipid was dissolved by adding 250 mL of ethanol and again subjected to the removal of the ethanol solvent according to the ordinary method to prepare an RI-labeled lipid membrane. According to an ordinary method, 250 μL of 10 mmol/L HEPES buffer (pH 7.4) prepared using HEPES (WAKO Pure Chemical Industries Ltd.) was added to the lipid membrane, which was allowed to stand at room temperature for 15 minutes for hydration, followed by performing sonication for 30 seconds using a sonicator to prepare each of the following RI-labeled peptide-PEG modified liposomes.

Liposome containing 5% of the modified lipid 1; RI/1-PEG
Liposome containing 5% of the modified lipid 2; RI/2-PEG
Liposome containing 5% of the modified lipid 3; RI/3-PEG
Liposome containing 5% of the modified lipid 4; RI/4-PEG
Liposome containing 5% of the modified lipid 5; RI/5-PEG
Liposome containing 5% of the modified lipid 6; RI/6-PEG (comparative example)

[4-2] Identification of Size of RI-Labeled Peptide-PEG Modified Liposome

When an RI-unlabeled peptide-PEG modified liposome containing no RI was prepared according to the method described in (4) [4-1] of this Example and measured for size using a dynamic light scattering measurement apparatus (ZETASIZER Nano ZS; MALVERN), the liposome was found to have a diameter of about 100 nm. This demonstrated that the RI-labeled peptide-PEG modified liposome prepared in (4) [4-1] of this Example had a size of about 100 nm in diameter.

[4-3] Preparation of RI-Labeled PEG Modified Liposome

PEG2000-DSPE {product name: 1,2-distearoyl-snGlycero-3-Phosphoethanolamine-N-[Carboxy(Polyethylene Glycol)2000] (Ammonium Salt), corporate name: Avanti Polar Lipids} was used in place of the peptide-PEG modified lipid to prepare RI/PEG (comparative example) as an RI-labeled PEG modified liposome according to the method described in (4) [4-1] of this Example. An RI-labeled lipid membrane was prepared according to the method described in (4) [4-1] of this Example, and subsequently, 250 μL of 10 mmol/L HEPES buffer (pH 7.4) prepared according to an ordinary method using HEPES (WAKO Pure Chemical Industries Ltd.) was then added to the lipid membrane, which was then allowed to stand at room temperature for 15 minutes for hydration and further mixed by shaking by hand several times to prepare RI/800PEG (comparative example) which was an RI-labeled PEG modified liposome having a microsize of about 800 nm in diameter.

[4-4] Preparation of RI-Labeled Peptide Modified Liposome

The following peptide modified fatty acids in which stearic acid (STR) was added to the C-terminal ends of K8 (KKKKKKKK; SEQ ID N: 7) as a cationic peptide inducing the intracellular incorporation of a substance via proteoglycan (see "Ayman El-Sayed et al., J. Biol. Chem., 283 (34): 23450-23461" for the induction of intracellular incorporation and "Christine K. Payne et al., Traffic, 8: 389-401" for the intracellular incorporation of a cationic substance via proteoglycan) and the peptide 1 selected in (2) of this Example were purchased from KUROBO.

```
Modified Fatty Acid 1;  LRQRRRL (SEQ ID NO: 1)-STR

Modified Fatty Acid 7;  KKKKKKKK (SEQ ID NO: 7)-STR
```

The prepared modified fatty acid 1 and modified fatty acid 7 were used to prepare the following liposomes modified with the peptides not via PEG according to the method described in (4) [4-1] of this Example.

Liposome containing 5% of the modified fatty acid 1; RI/1
Liposome containing 5% of the modified fatty acid 7; RI/7 (comparative example)

[4-5] Preparation of RI-Labeled Cationic Liposome 1,2-dioleoyl-3-trimethylammonium-propane (DOTAP; Avanti Polar Lipids) as a cationic lipid and 1,2-dioleoyl-sn-glycero-3-phosphoethanolamine (DOPE; Avanti Polar Lipids) were mixed to DOTAP:DOPE=3:7 to prepare a mixed lipid powder. Subsequently, the prepared mixed lipid powder was dissolved in ethanol to 1 nmol/μL, and 137.5 μL of the resultant was placed in a glass test tube, followed by preparing RI/DOTAP/DOPE as an RI-labeled cationic liposome by the method described in (4) [4-1] of this Example.

[4-6] Preparation of Fluorescence-Labeled Peptide 1 Modified Liposome

Rho/1-PEG as an RI-unlabeled fluorescence-labeled peptide 1 modified liposome was prepared using the method described in (4) [4-1] of this Example by setting the mol % ratio of the mixed lipid:the modified lipid 1 prepared in (3) of this Example: a rhodamine-bound lipid (Rhodamine-DOPE; Phosphoethanolamine-N-Lissamine Rhodamine B Sulfonyl, [1,2-Dioleoyl-sn-Glycero-3-], Ammonium Salt (Chloroform), Avanti Polar Lipids) in which rhodamine was bound to DOPE to 90:5:5 in place of setting the mol % ratio of the mixed lipid:the modified lipid prepared in (3) of this Example to 95:5.

[4-7] Preparation of Fluorescence-Labeled DOTAP/DOPE Liposome

DOTAP (Avanti Polar Lipids), DOPE (Avanti Polar Lipids), and Rhodamine-DOPE (Avanti Polar Lipids) were mixed to DOTAP:DOPE:Rhodamine-DOPE=30:65:5 to prepare a mixed lipid powder. Subsequently, the prepared mixed lipid powder was dissolved in ethanol to 1 nmol/μL and 137.5 μL of the resultant was placed in a glass test tube, followed by preparing Rho/DOTAP/DOPE as a fluorescence-labeled DOTAP/DOPE liposome by the method described in (4) [4-1] of this Example without adding RI.

Example 2

Examination of Cell Permeation Ratio of RI-Labeled Modified Liposome (1) Calculation of Cell-Free Permeation Rate of Liposome In the area on the side of the upper layer in a device for evaluating cell permeability (Japanese Patent Application No. 2009-275877) was placed 100 μL/well of the Krebs buffer prepared in (1) of Example 1, to which 100 μL (about 1,000,000 to 2,000,000 dpm)/well of each of the RI/1-PEG, RI/2-PEG, RI/3-PEG, RI/4-PEG, RI/5-PEG, and RI/6-PEG prepared in (4) [4-1] of Example 1, the RI/PEG and RI/800PEG prepared in (4) [4-3] of Example 1, and the RI/1 and RI/7 prepared in (4) [4-4] of Example 1 was further added. After 2 hours, the Krebs buffer was recovered from the area on the side of the lower layer, and the amount of RI contained in the recovered Krebs buffer was measured using a liquid scintillation counter, TRI/CARB 1600TR (Packard). The ratio of the measured RI amount was calculated as the percentage of the RI amount of the liposome added to the area on the upper layer side and defined as the liposome permeation rate when cells were not cultured in the device for evaluating cell permeability (Japanese Patent Application No. 2009-275877) (cell-free liposome permeation rate).

(2) Calculation of Cell-Laden Permeation Rate of Liposome

[2-1] Culture of MBEC4 Cell

MBEC4 cells derived from mouse brain capillary endothelial cells (a gift from Takashi Tsuruo and Mikihiko Naito, Institute of Molecular and Cellular Biosciences, The University of Tokyo) was suspended in Dulbecco's Modified Eagle's Medium (DMEM medium) to 300,000 cells/mL. The suspension was placed in the area on the side of the upper layer in the device for evaluating cell permeability (Japanese Patent Application No. 2009-275877) to 400 μL/well and subjected to standing culture at 37° C. for 3 to 5 days under a 5% $CO_2$ atmosphere until the cultured cells formed the tight junction therebetween. Whether the cells formed the tight junction or not was confirmed by the measurement of transmembrane electric resistance (TER) using MILLICELL-ERS (MILLIPORE).

[2-2] Calculation of Cell-Laden Permeation Rate of Liposome

The culture medium of cells cultured in (2) [2-1] of this Example was removed, and the cells were washed once with the Krebs buffer prepared in (1) of Example 1, followed by adding the Krebs buffer in the same amount as that of the removed culture medium and further adding 100 μL (about 1,000,000 to 2,000,000 dpm)/well of each of the RI/1-PEG, RI/2-PEG, RI/3-PEG, RI/4-PEG, RI/5-PEG, and RI/6-PEiG prepared in (4) [4-1] of Example 1, the RI/PEG and RI/800PEG prepared in (4) [4-3] of Example 1, and the RI/1 and RI/7 prepared in (4) [4-4] of Example 1. Then, the liposome permeation rate when cells were cultured in the device for evaluating cell permeability (cell-laden liposome permeation rate) was calculated by the method described in (1) of this Example.

(3) Calculation of Cell Permeation Ratio of RI-Labeled Modified Liposome

The cell permeation ratio of each of the RI/1-PEG, RI/2-PEG, RI/3-PEG, RI/4-PEG, RI/5-PEG, and RI/6-PEG prepared in (4) [4-1] of Example 1, the RI/PEG and RI/800PEG prepared in (4) [4-3] of Example 1, and the RI/1 and RI/7 prepared in (4) [4-4] of Example 1 was calculated by the following equation. In addition, a t-test was performed for RI/1-PEG determined to have the highest cell permeation ratio as a result of the calculation. The results are shown in FIG. 1.

Cell permeation ratio=the cell-laden liposome permeation rate calculated in (2) of this Example/the cell-free liposome permeation rate calculated in (1) of this Example.

Figure 1:
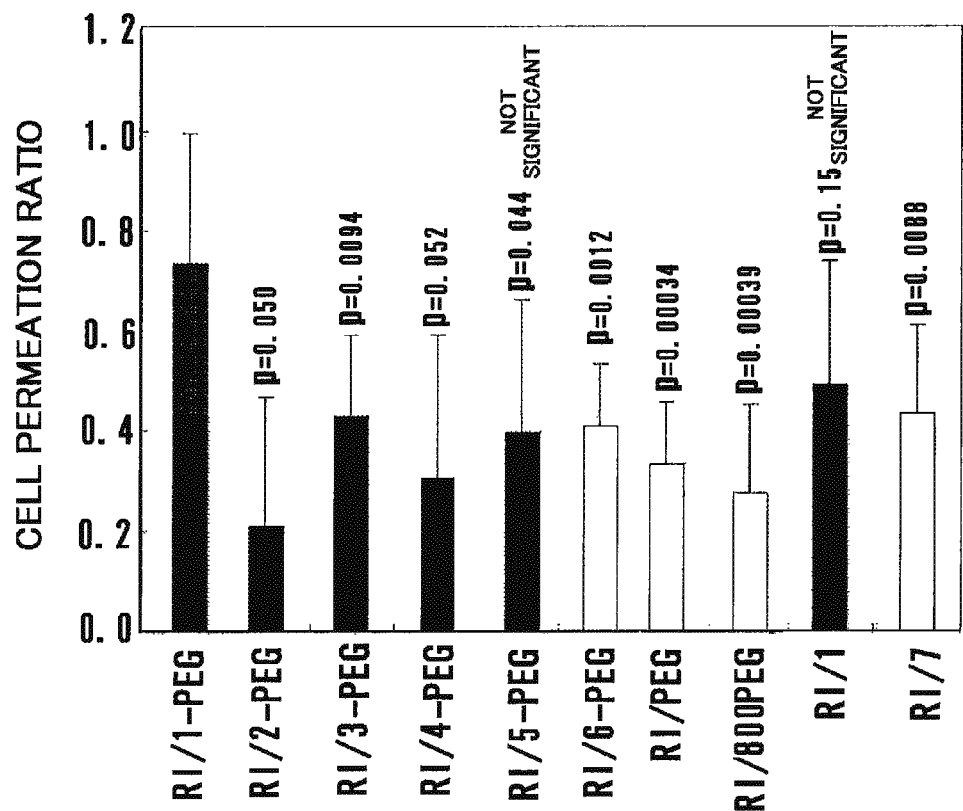
FIG. 1 is a graph showing the cell permeation ratios of a liposome modified with a peptide via PEG (RI/1-PEG, RI/2-

FIG. 1 showed that RI/1-PEG had a highest cell permeation ratio of about 0.72 and RI/1 had a second highest cell permeation ratio of about 0.49 although no significant difference was found between RI/1 and RI/1-PEG. It was also shown that the cell permeation ratios of RI/1-PEG and RI/1 were higher than the cell permeation ratios of RI/6-PEG and RI/7, which were modified with R8 and K8 known to impart certain intracellular migration ability to liposomes. Meanwhile, the results were obtained that RI/3-PEG and RI/5-PEG had almost the same cell permeation ratios as the cell permeation ratios of RI/6-PEG and RI/7 and RI/2-PEG had the lowest cell permeation ratio. RI/4-PEG had a cell permeation ratio not significantly different compared to that of RI/1-PEG but a low cell permeation ratio comparable with those of the peptide-unmodified RI/PEG and the large-sized RI/800PEG.

These results demonstrated that the peptide 1 selected in (2) of Example 1 was excellent in imparting cell permeability to liposomes and enhancing cell permeability of liposomes.

Example 3

Examination of Need for PEG in Intracellular Incorporation of RI/1-PEG

MBEC4 cells were cultured on a petri dish by the method described in (2) [2-1] of Example 2, followed by removing the culture medium and washing once using the Krebs buffer prepared in (1) of Example 1. Subsequently, the Krebs buffer was added in the same amount as that of the removed culture medium thereto, to which 100 μL (about 1,000,000 to 2,000,000 dpm)/well of each of the RI/1-PEG prepared in (4) [4-1] in Example 1 and the RI/1 prepared in (4) [4-4] of Example 1 was then added. After 2 hours, the liposome-containing Krebs buffer was removed, followed by washing 3 times using 1 mL of PBS (Nissui Pharmaceutical Co., Ltd.) containing 40 units/mL heparin (WAKO Pure Chemical Industries Ltd.). Subsequently, the resultant was immersed in a 3N NaOH aqueous solution overnight to lyse cells, and the amount of RI in the cell lysate was measured using a liquid scintillation counter, TRI/CARB 1600TR (Packard). The ratio of the measured RI amount to the added RI amount was calculated in percentage as the ratio of intracellular incorporation of liposomes. The results are shown in FIG. 2.

FIG. 2 showed that the ratio of intracellular incorporation of RI/1-PEG was large compared to the ratio of intracellular incorporation of RI/1. This result demonstrated that many liposomes modified with the peptide 1 via PEG were incorporated into MBEC4 cells compared to liposomes modified with the peptide 1 not via PEG.

Example 4

Examination of Involvement of Lipid Raft in Cell Permeation and Intracellular Incorporation of RI/1-PEG (1) Examination of Involvement of Lipid Raft in Cell Permeation The cell permeation ratio of the RI/1-PEG prepared in (4) [4-1] of Example 1 was calculated according to the method described in Example 2. In calculating the cell-free permeation rate of liposomes and the cell-laden permeation rate of liposomes, the Krebs buffer prepared in (1) of Example 1 was placed in wells, and at the same time Filipin III (SIGMA) as a reagent for specifically binding to cholesterol to inhibit the function of lipid raft was added to 5 μmol/L or 15 μmol/L thereto, which was then incubated for 1 hour, followed by adding RI/1-PEG.

Subsequently, the proportions of the cell permeation ratio of RI/1-PEG calculated when Filipin III was added to 5 μmol/L or 15 μmol/L to the cell permeation ratio of RI/1-PEG calculated in (3) of Example 2 (the cell permeation ratio when Filipin III was not added) was calculated in percentage. The calculated values were subjected to a t-test as compared to those of the cell permeation ratio of RI/1-PEG (the cell permeation ratio of RI/1-PEG when Filipin III was not added) calculated in (3) of Example 2. The results are shown in FIG. 3.

As shown in FIG. 3, the addition of 5 μmol/L of Filipin III reduced, but not significantly, the proportion of the cell permeation ratio to about 60% compared to no addition thereof and the addition of 15 μmol/L thereof reduced the proportion of the cell permeation ratio to about 35%. In other words, it was shown that the cell permeation ratio and the proportion of the cell permeation ratio were reduced proportionally with increasing amount of Filipin III added.

These results demonstrated that RI/1-PEG was mainly passed through cells via lipid raft.

(2) Examination of Involvement of Lipid Raft in Intracellular Incorporation

The intracellular incorporation ratios of the RI/1-PEG prepared in (4) [4-1] of Example 1 and the RI/1 prepared in (4) [4-4] of Example 1 were calculated according to the method described in Example 3. When the Krebs buffer prepared in (1) of Example 1 was placed in a petri dish, Filipin III (SIGMA) as a reagent for inhibiting lipid raft was simultaneously added to 5 μmol/L or 15 μmol/L, and the mixture was incubated for 1 hour, followed by adding each of RI/1-PEG and RI/1 thereto.

Subsequently, the proportion of the intracellular incorporation ratio of RI/1-PEG calculated when Filipin III was added to the intracellular incorporation ratio of RI/1-PEG calculated in Example 3 (the intracellular incorporation ratio of RI/1-PEG when Filipin III was not added) was calculated in percentage. The calculated values were subjected to a t-test as compared to those of the intracellular incorporation ratio of RI/1-PEG (the intracellular incorporation ratio of RI/1 when Filipin III was not added) calculated in Example 3. Similarly, the proportion of the intracellular incorporation ratio of RI/1 calculated when Filipin III was added to the intracellular incorporation ratio of RI/1 calculated in Example 3 (the intracellular incorporation ratio of RI/1-PEG when Filipin III was not added) was calculated in percentage, and the calculated values were subjected to a t-test as compared to those of the intracellular incorporation ratio of RI/1 (the intracellular incorporation of RI/1 when Filipin III was not added) calculated in Example 3. The results are shown in FIG. 4.

As shown in FIG. 4, the addition of 5 μmol/L of Filipin III reduced the proportion of the intracellular incorporation ratio of RI/1-PEG to about 73% as compared to that when Filipin III was not added, and the addition of 15 μmol/L thereof reduced the proportion of the intracellular incorporation ratio of RI/1-PEG to about 50% as compared to that when Filipin III was not added. In other words, it was shown that the intracellular incorporation ratio and the proportion of the intracellular incorporation ratio were reduced proportionally with increasing amount of Filipin III added. In contrast, the addition of 5 μmol/L of Filipin III increased, but not significantly, the proportion of the intracellular incorporation ratio of RI/1 to about 142% as compared to that when Filipin III was not added, and the addition of 15 μmol/L thereof increased, but not significantly, the intracellular incorporation ratio of RI/1 to about 180% as compared to that when Filipin III was not added.

These results demonstrated that RI/1-PEG was mainly incorporated into cells via lipid raft and RI/1 was mainly incorporated into cells through a pathway not via the lipid raft.

Example 5

Examination of Important Amino Acid Sequence in Peptide 1

The following peptides obtained by changing the amino acid sequence of the peptide 1 were prepared by chemical synthesis under commission to Hokkaido System Science Co., Ltd. The changed portions of the amino acid sequence of the peptide 1 were underlined. The peptides 8 to 13 are peptides obtained by changing at least one of the N-terminal and C-terminal amino acids of the amino acid sequence of the peptide 1; the peptide 14 is a peptide obtained by changing R at the 2nd position from the N-terminal end of the amino acid sequence of the peptide 1 to L; the peptide 15 is a peptide obtained by changing all Rs of the amino acid sequence of the peptide 1 to Ks; the peptides 16 and 17 are peptides obtained by increasing R at the 2nd position from the N-terminal end of the amino acid sequence of the peptide 1; the peptides 18 and 19 are peptides obtained by changing Q at the 3rd position from the N-terminal end of the amino acid sequence of the peptide 1 to R or A, respectively; the peptides 20 and 21 are peptides obtained by changing the position of Q at the 3rd position from the N-terminal end of the amino acid sequence of the peptide 1 while holding Ls at the N-terminal and C-terminal ends thereof; the peptides 22 and 23 are peptides obtained by adding L or R, respectively, at both terminal ends of the amino acid sequence of the peptide 1 to change the length of the peptide; the peptides 24 and 25 are peptides obtained by changing the alignment of the amino acid sequence of the peptide 1; the peptides 26 to 29 are peptides obtained by decreasing or increasing the number of Rs at the 4th to 6th positions from the N-terminal end of the amino acid sequence of the peptide 1; the peptides 30 to 32 are peptides obtained by adding L or A C-terminal to R at the 6th position from the N-terminal end of the amino acid sequence of the peptide 1; and the peptides 33 to 37 are peptides obtained by changing R at the 4th to 6th positions from the N-terminal end of the amino acid sequence of the peptide 1.

| Peptide 8; | RRQRRRL | (SEQ ID NO. 8) |
| Peptide 9; | LRQRRRR | (SEQ ID NO. 9) |
| Peptide 10; | RRQRRRR | (SEQ ID NO. 10) |
| Peptide 11; | SRQRRRS | (SEQ ID NO. 11) |
| Peptide 12; | IRQRRRI | (SEQ ID NO. 12) |
| Peptide 13; | VRQRRRV | (SEQ ID NO. 13) |
| Peptide 14; | LLQRRRL | (SEQ ID NO. 14) |
| Peptide 15; | LKQKKKL | (SEQ ID NO. 15) |
| Peptide 16; | LRRQRRRL | (SEQ ID NO. 16) |
| Peptide 17; | LRRRQRRRL | (SEQ ID NO. 17) |
| Peptide 18; | LRRRRRL | (SEQ ID NO. 18) |
| Peptide 19; | LRARRRL | (SEQ ID NO. 19) |
| Peptide 20; | LRRQRRL | (SEQ ID NO. 20) |
| Peptide 21; | LRRRQRL | (SEQ ID NO. 21) |
| Peptide 22; | LLRQRRRLL | (SEQ ID NO. 22) |
| Peptide 23; | RLRQRRRLR | (SEQ ID NO. 23) |
| Peptide 24; | QRRLLRR | (SEQ ID NO. 24) |
| Peptide 25; | RRLLQRR | (SEQ ID NO. 25) |
| Peptide 26; | LRQRRL | (SEQ ID NO. 26) |
| Peptide 27; | LRQRL | (SEQ ID NO. 27) |
| Peptide 28; | LRQRRRRL | (SEQ ID NO. 28) |
| Peptide 29; | LRQRRRRRL | (SEQ ID NO. 29) |
| Peptide 30; | LRQRRRLL | (SEQ ID NO. 30) |
| Peptide 31; | LRQRRRAL | (SEQ ID NO. 31) |
| Peptide 32; | LRQRRRAAL | (SEQ ID NO. 32) |
| Peptide 33; | LRQRLRL | (SEQ ID NO. 33) |
| Peptide 34; | LRQLRRL | (SEQ ID NO. 34) |
| Peptide 35; | LRQSSSL | (SEQ ID NO. 35) |
| Peptide 36; | LRQRRDL | (SEQ ID NO. 36) |
| Peptide 37; | LRQRDDL | (SEQ ID NO. 37) |

For the peptides 8 to 37, peptide-PEG modified lipids were prepared according to the method described in (3) of Example 1, followed by preparing the following RI-labeled peptide-PEG modified liposomes according to the method described in (4) [4-1] of Example 1.

Liposome containing 5% of peptide 8-PEG-modified lipid; RI/8-PEG
Liposome containing 5% of peptide 9-PEG-modified lipid; RI/9-PEG
Liposome containing 5% of peptide 10-PEG-modified lipid; RI/10-PEG
Liposome containing 5% of peptide 11-PEG-modified lipid; RI/11-PEG
Liposome containing 5% of peptide 12-PEG-modified lipid; RI/12-PEG
Liposome containing 5% of peptide 13-PEG-modified lipid; RI/13-PEG
Liposome containing 5% of peptide 14-PEG-modified lipid; RI/14-PEG
Liposome containing 5% of peptide 15-PEG-modified lipid; RI/15-PEG
Liposome containing 5% of peptide 16-PEG-modified lipid; RI/16-PEG
Liposome containing 5% of peptide 17-PEG-modified lipid; RI/17-PEG
Liposome containing 5% of peptide 18-PEG-modified lipid; RI/18-PEG
Liposome containing 5% of peptide 19-PEG-modified lipid; RI/19-PEG
Liposome containing 5% of peptide 20-PEG-modified lipid; RI/20-PEG
Liposome containing 5% of peptide 21-PEG-modified lipid; RI/21-PEG
Liposome containing 5% of peptide 22-PEG-modified lipid; RI/22-PEG
Liposome containing 5% of peptide 23-PEG-modified lipid; RI/23-PEG
Liposome containing 5% of peptide 24-PEG-modified lipid; RI/24-PEG
Liposome containing 5% of peptide 25-PEG-modified lipid; RI/25-PEG
Liposome containing 5% of peptide 26-PEG-modified lipid; RI/26-PEG
Liposome containing 5% of peptide 27-PEG-modified lipid; RI/27-PEG
Liposome containing 5% of peptide 28-PEG-modified lipid; RI/28-PEG
Liposome containing 5% of peptide 29-PEG-modified lipid; RI/29-PEG
Liposome containing 5% of peptide 30-PEG-modified lipid; RI/30-PEG
Liposome containing 5% of peptide 31-PEG-modified lipid; RI/31-PEG
Liposome containing 5% of peptide 32-PEG-modified lipid; RI/32-PEG
Liposome containing 5% of peptide 33-PEG-modified lipid; RI/33-PEG
Liposome containing 5% of peptide 34-PEG-modified lipid; RI/34-PEG
Liposome containing 5% of peptide 35-PEG-modified lipid; RI/35-PEG
Liposome containing 5% of peptide 36-PEG-modified lipid; RI/36-PEG
Liposome containing 5% of peptide 37-PEG-modified lipid; RI/37-PEG Subsequently, the cell permeation rates of these liposomes were calculated according to the method described in Example 2, and the proportion of each of the calculated cell permeation ratios to the cell permeation ratio of RI/1-PEG calculated in (3) of Example 2 was calculated in percentage. The results of RI/8-PEG to RI/13-PEG are shown in FIG. 5; the results of RI/14-PEG to RI/17-PEG, in FIG. 6; the results of RI/18-PEG and RI/19-PEG, in FIG. 7; the results of RI/20-PEG and RI/21-PEG, in FIG. 8; the results of RI/22-PEG and RI/23-PEG, in FIG. 9; the results of RI/24-PEG and RI/25-PEG, in FIG. 10; the results of RI/26-PEG and RI/27-PEG, in FIG. 11; the results of RI/28-PEG to RI/32-PEG, in FIG. 12; and the results of RI/33-PEG to RI/37-PEG, in FIG. 13.

As shown in FIGS. 5 and 10, the proportions of the cell permeation ratios of RI/8-PEG, RI/9-PEG, RI/10-PEG, RI/11-PEG, RI/12-PEG, RI/13-PEG, RI/24-PEG, and RI/25-PEG were about 38.5%, about 40%, about 6.2%, about 39%, about 21.5%, about 24.6%, about 30%, and about 20%, respectively. These results demonstrated that when the peptides were each a heptapeptide and the N-terminal amino acid residue and the C-terminal amino acid residue were both L, the cell permeability of each liposome was enhanced.

As shown in FIG. 6, the proportions of the cell permeation ratios of RI/14-PEG, RI/16-PEG, and RI/17-PEG were about 60%, about 6%, and about 4%, respectively. These results demonstrated that when the peptides were each a heptapeptide and the amino acid residue at the 2nd position from the N-terminal end thereof was L or a polar amino acid residue, the cell permeability of each liposome was enhanced.

As shown in FIGS. 7, 8, and 10, the proportions of the cell permeation ratios of RI/18-PEG, RI/19-PEG, RI/20-PEG, RI/21-PEG, RI/24-PFG, and RI/25-PEG were about 10%, about 44.6%, about 33.8%, about 10%, about 30%, and about 20%, respectively. These results demonstrated that when the peptides were each a heptapeptide and the amino acid residue at the 3rd position from the N-terminal end thereof was a polar, non-charged and branched chain amino acid residue, the cell permeability of each liposome was enhanced.

As shown in FIGS. 6, 9, and 12, the proportions of the cell permeation ratios of RI/16-PEG, RI/17-PEG, RI/22-PEG, RI/23-PEG, RI/28-PEG, RI/29-PEG, RI/30-PEG, RI/31-PEG, and RI/32-PEG were about 6%, about 4%, about 12.3%, about 2.3%, about 16.7%, about 6.7%, about 38.3%, about 8.3%, and about 5%, respectively. These results demonstrated that when the peptides were each 8 amino acid residues long or more, the cell permeability of each liposome was reduced.

As shown in FIG. 10, the proportions of the cell permeation ratios of RI/24-PEG and RI/25-PEG were about 30% and about 20%, respectively. These results demonstrated that the heptapeptides obtained by changing the alignment of the amino acid sequence of the peptide 1 reduced the cell permeability of each liposome.

As shown in FIG. 11, the proportions of the cell permeation ratios of RI/26-PEG and RI/27-PEG were about 60% and about 47%, respectively. These results demonstrated that the heptapeptides in each of which the N-terminal and C-terminal ends were L, the amino acid residue at the 2nd position from the N-terminal end was a polar amino acid residue, and the amino acid at the 3rd position from the N-terminal end was a polar, non-charged and branched chain amino acid residue reduced the cell permeability of each liposome.

As shown in FIGS. 6, 12, and 13, the proportions of the cell permeation ratios of RI/15-PEG, RI/28-PEG, RI/29-PEG, RI/30-PEG, RI/31-PEG, RI/32-PEG, RI/33-PEG, RI/34-PEG, RI/36-PEG, and RI/37-PEG were about 109%, about 16.7%, about 6.7%, about 38.3%, about 8.3%, about 5%, about 13%, about 36%, about 98%, about 49%, and about 80%, respectively; thus, it was demonstrated that when the peptide was a hexapeptide or a heptapeptide and the 2 or 3 amino acid residues between the polar, non-charged and branched chain amino acid residue at the 3rd position from the N-terminal end and L at the C-terminal end are polar amino acid residues, the cell permeability of each liposome was markedly enhanced.

As shown in FIG. 12, the proportions of the cell permeation ratios of RI/30-PEG, RI/31-PEG, and RI/32-PEG were about 38.3%, about 8.3%, and about 5%; thus, it was demonstrated that the addition of L or A C-terminal to R at the 6th position from the N-terminal end of the amino acid sequence of the peptide 1 reduced the cell permeability of each liposome.

Example 6

Examination of Peptide Amount for Modification

For the peptide 1, RI-labeled peptide-PEG modified liposomes were prepared according to the method described in (4) [4-1] of Example 1. However, when the mixed lipid ethanol solution and the peptide-PEG modified lipid aqueous solution were placed in a glass test tube, three types of combinations were provided in which the mol % ratios of (the mixed lipid):(the peptide-PEG modified lipid prepared in (3) of Example 1) were 99:1, 95:5, and 90:10. That is, three types of liposomes having mol % ratios of the peptide 1 modified lipid of 1%, 5%, and 10% were prepared and called RI/1-PEG (1%), RI/1-PEG (5%), and RI/1-PEG (10%), respectively. The cell permeation ratios of these liposomes were calculated by the method described in Example 2. The calculated values were subjected to a t-test as compared to those of the cell permeation ratio of RI/1-PEG (5%). The results are shown in FIG. 14.

As shown in FIG. 14, the cell permeation ratios of RI/1-PEG (1%), RI/1-PEG (5%), and RI/1-PEG (10%) were about 0.42, about 0.73, and about 0.54, respectively, and the cell permeation ratio of RI/1-PEG (5%) was highest, although no significant difference was observed. These results demonstrated that the cell permeation rate was highest when the percentage of the peptide 1 modified lipid was 5 mol %.

Example 7

Examination of Intracellular Incorporation Ratio of Liposome in Inhibition of Intracellular Incorporation via Heparan Sulfate Proteoglycan (HSPG)

(1) Heparin Treatment of Liposome

To 0.01 mL of each of solutions of the RI/1-PEG prepared in (4) [4-1] of Example 1, the RI/7 prepared in (4) [4-4] of Example 1, and the RI/DOTAP/DOPE prepared in (4) [4-5] of Example 1 was added 100 units of heparin (WAKO Pure Chemical Industries Ltd.) having the effect of competitively inhibiting heparan sulfate proteoglycan (HSPG), which was incubated at room temperature for 15 minutes for the heparin treatment of each liposome.

(2) Measurement of Intracellular Incorporation Ratio of Liposome Treated with Heparin The intracellular incorporation ratios of the RI/1-PEG, RI/7, and RI/DOTAP/DOPE treated with heparin in (1) of this Example were measured by the method described in Example 3. Simultaneously, the intracellular incorporation ratios of the RI/1-PEG prepared in (4) [4-1] of Example 1, RI/7 prepared in (4) [4-4] of Example 1, and RI/DOTAP/DOPE prepared in (4) [4-5] of Example 1 not subjected to the heparin treatment of (1) of this Example were calculated as controls by the same method to calculate, in percentage, the proportions of the intracellular incorporation ratios when the heparin treatment was performed to the cellular incorporation ratios of the control liposomes. The results are shown in FIG. 15.

FIG. 15 showed that the proportion of the intracellular incorporation ratio of RI/1-PEG was about 15.4% and markedly reduced compared to that when the heparin treatment was not performed. The proportion of the intracellular incorporation ratio of RI/DOTAP/DOPE was shown to be about 93.8% and little changed as compared to that when the heparin treatment was not performed. The proportion of the intracellular incorporation ratio of RI/7 was shown to be about 75.4% and slightly reduced as compared to that when the heparin treatment was not performed.

When liposomes are intracellularly incorporated via HSPG on the cell surface, the treatment of the liposomes with heparin having a structure similar to HSPG reduces the intracellular incorporation ratio of the liposomes. Thus, the above results confirmed that RI/1-PEG was mainly intracellularly incorporated via HSPG. It was also confirmed that RI/DOTAP/DOPE and RI/7 having cationicity like RI/1-PEG were mainly intracellularly incorporated through a pathway not via HSPG.

Example 8

Checking of State of Intracellular Incorporation of Rho/1-PEG (1) Heparin Treatment of Liposome The Rho/1-PEG prepared in (4) [4-6] of Example 1 and the Rho/DOTAP/DOPE prepared in (4) [4-7] of Example 1 were treated with heparin by the method described in (1) of Example 7.

(2) Checking of State of Intracellular Incorporation of Liposome by Fluorescent Microscopic Observation Cells were cultured on a glass base dish (IWAKI) by the method described in (2) [2-1] of Example 2; the culture medium was then removed; the resultant was washed once with the Krebs buffer prepared in (1) of Example 1; the Krebs buffer was added in the same amount as that of the removed culture medium; and 100 µL (about 1,000,000 to 2,000,000 dpm)/well of each of the Rho/1-PEG and Rho/DOTAP/DOPE treated with heparin in (1) of this Example was added thereto. After 1 hour, the liposome-containing Krebs buffer was removed, and the residue was washed three times with 1 mL of PBS (Nissui Pharmaceutical Co., Ltd.) containing 40 units/mL heparin (WAKO Pure Chemical Industries Ltd.) and then subjected to the observation of rhodamine fluorescence using a microscope with a camera (camera: Hamamatsu Photonics K.K., Microscope: Nikon Corporation). Simultaneously, the Rho/1-PEG prepared in (4) [4-6] of Example 1 and the Rho/DOTAP/DOPE prepared in (4) [4-7] of Example 1 both not subjected to the heparin treatment of (1) of this Example were each incorporated into cells and subjected to fluorescent observation by the same method as a control. The results are shown in FIG. 16.

As shown in FIG. 16, for Rho/1-PEG, rhodamine fluorescence was observed in the cells in the control, whereas the rhodamine fluorescence was little observed in the cells in the heparin treatment. For Rho/DOTAP/DOPE, the rhodamine fluorescence was observed in the cells as in the control even in the heparin treatment.

These results confirmed that Rho/1-PEG was mainly intracellularly incorporated via HSPG. It was also confirmed that Rho/DOTAP/DOPE having cationicity like Rho/1-PEG was mainly intracellularly incorporated through a pathway not via HSPG.

Example 9

Identification of Transport Pathway for Rho/1-PEG Liposome in Vascular Endothelial Cell and Non-Vascular Endothelial Cell (1) Labeling of Early Endosome in Cell An expression plasmid encoding a fused protein of Rab5 as a low molecular weight GTP-binding protein localized in early endosomes and GFP as a green fluorescent protein (Rab5-GFP) was prepared in advance, and, 24 hours before performing fluorescent observation in (4) of this Example to be described later, the gene was introduced into MBEC4 cells and CHO-K1 cells (Chinese hamster ovary cells) as non-vascular endothelial cells on which HSPG was known to be expressed, using a cationic lipid (Lipofectamine PLUS, INVITROGEN) for gene introduction to fluorescently label the early endosomes.

(2) Labeling of Late Endosome in Cell

An expression plasmid encoding a fused protein of Rab7 as a low molecular weight GTP-binding protein localized in late endosomes and GFP (Rab7-GFP) was prepared in advance, and, 24 hours before performing fluorescent observation in (4) of this Example to be described later, the gene was introduced into MBEC4 cells and CHO-K1 cells using a cationic lipid (Lipofectamine PLUS, INVITROGEN) for gene introduction to fluorescently label the late endosomes.

(3) Labeling of *Lysosome* in Cell

LysoTracker Blue DND-22 (INVITROGEN) was added to the medium of each of the MBEC4 cells in which early endosomes were fluorescently labeled in (1) of this Example, the CHO-K1 cells in which early endosomes were fluorescently labeled in (1) of this Example, the MBEC4 cells in which late endosomes were fluorescently labeled in (2) of this Example, and the CHO-K1 cells in which late endosomes were fluorescently labeled in (2) of this Example, according to the appended instructions, which was then incubated for 30 minutes to fluorescently label lysosomes.

(4) Identification of Incorporation Pathway for Liposome by Fluorescent Microscopic Observation The Rho/1-PEG prepared in (4) [4-6] of Example 1 was incorporated into each cells in which lysosomes were fluorescently labeled in (3) of this Example by the method described in (2) of Example 8 to observe rhodamine, GFP, and LysoTracker Blue fluorescence. The results of observing MBEC4 cells are shown in FIG. 17, and the results of observing CHO-K1 cells are shown in FIG. 18.

As shown in FIG. 17, rhodamine fluorescence was observed at different locations from those at which each of GFP fluorescence and LysoTracker Blue fluorescence was observed, in MBEC4 cells whose early endosomes were fluorescently labeled. Similarly, rhodamine fluorescence was observed at different locations from those at which each of GFP fluorescence and LysoTracker Blue fluorescence was observed, in MBEC4 cells whose late endosomes were fluorescently labeled. These results showed that the Rho/1-PEG incorporated into MBEC4 cells was passed through cells without being transferred to early endosomes, late endosomes, or lysosomes.

As shown in FIG. 18, rhodamine fluorescence was observed at different locations from those at which GFP fluorescence was observed and at the same locations indicated by arrows as those at which LysoTracker Blue fluorescence was observed, in CHO-K1 cells whose early endosomes were fluorescently labeled. In addition, it was observed at different locations from those at which LysoTracker Blue fluorescence was observed and at the same locations indicated by arrows as those at which GFP fluorescence was observed, in CHO-K1 cells whose late endosomes were fluorescently labeled. These results showed that in CHO-K1 cells, the intracellularly incorporated Rho/CI95-PEG was transferred to lysosomes and late endosomes, suggesting that it entered an ordinary degradation system without being passed through the cells.

The invention claimed is:

1. A method for imparting cell permeability to or enhancing cell permeability of a lipid membrane structure, comprising binding a peptide to the lipid membrane structure, wherein the peptide consists of an amino acid sequence selected from the group consisting of $LX_1X_2X_1X_1X_1L$, $LLX_2X_1X_1X_1L$, LRQRRL (SEQ ID NO: 26), LKQKKL (SEQ ID NO: 39), LRQSSL (SEQ ID NO: 41), and LRQRDL (SEQ ID NO: 43), wherein L represents a leucine residue, R represents an arginine residue, Q represents a glutamine residue, K represents a lysine residue, S represents a serine residue, D represents an aspartic acid residue, T represents a threonine residue, E represents a glutamic acid residue, and N represents an asparagine residue, $X_1$ represents a polar amino acid residue selected from the group consisting of S, T, D, E, R and K, and $X_2$ represents a polar, non-charged and branched chain amino acid residue selected from the group consisting of Q and N, wherein the amino acid sequence does not comprise LRQRRRL (SEQ ID NO: 1), whereby the cell permeability of the lipid membrane structure bound to the peptide is imparted or enhanced as compared with the lipid membrane not bound to the peptide.

2. The method according to claim 1, wherein the polar, non-charged and branched chain amino acid residue $X_2$ is Q, and wherein Q represents a glutamine residue.

3. The method according to claim 1, wherein the polar amino acid residues $X_1$ are the same or different amino acid residues selected from the group consisting of R, K, S, and D, and wherein R represents an arginine residue, K represents a lysine residue, S represents a serine residue, and D represents an aspartic acid residue.

4. The method according to claim 1, wherein the amino acid sequence is selected from the group consisting of LLQRRRL (SEQ ID NO: 14), LRQRRL (SEQ ID NO: 26), LKQKKKL (SEQ ID NO: 15), LRQRRDL (SEQ ID NO: 36), LLQKKKL (SEQ ID NO: 38), LKQKKL (SEQ ID NO: 39), LRQSSSL (SEQ ID NO: 35), LLQSSSL (SEQ ID NO: 40), LRQSSL (SEQ ID NO: 41), LRQRDDL (SEQ ID NO: 37), LLQRDDL (SEQ ID NO: 42), and LRQRDL (SEQ ID NO: 43).

5. A method for imparting cell permeability to or enhancing cell permeability of a lipid membrane structure, comprising binding a peptide to the lipid\membrane structure, wherein the peptide consists of an amino acid sequence selected from the group consisting of $LX_1X_2X_1X_1X_1L$, $LLX_2X_1X_1X_1L$, LRQRRL (SEQ ID NO: 26), LKQKKL (SEQ ID NO: 39), LRQSSL (SEQ ID NO: 41), and LRQRDL (SEQ ID NO: 43), wherein L represents a leucine residue, R represents an arginine residue, Q represents a glutamine residue, K represents a lysine residue, S represents a serine residue, D represents an aspartic acid residue, T represents a threonine residue, E represents a glutamic acid residue, and N represents an asparagine residue, $X_1$ represents a polar amino acid residue selected from the group consisting of S, T, D, E, R and K, and $X_2$ represents a polar, non-charged and branched chain amino acid residue selected from the group consisting of Q and N, wherein the amino acid sequence does not comprise LRQRRRL (SEQ ID NO: 1), whereby the cell permeability of the lipid membrane structure bound to the peptide is imparted or enhanced as compared with the lipid membrane not bound to the peptide, and wherein the peptide is further covalently bound to a tyrosine residue, a cysteine residue and a hydrophilic polymer in that physical order to the C-terminal end of the peptide.

6. The method according to claim 1, wherein the cell is an epithelial cell.

7. The method of claim 1, wherein the peptide is bound to a lipid molecule in the lipid membrane structure.

8. The method according to claim 7, wherein the polar, non-charged and branched chain amino acid residue $X_2$ is Q, and wherein Q represents a glutamine residue.

9. The method according to claim 7, wherein the polar amino acid residues $X_1$ are the same or different amino acid residues selected from the group consisting of R, K, S, and D, and wherein R represents an arginine residue, K represents a lysine residue, S represents a serine residue, and D represents an aspartic acid residue.

10. The method according to claim 7, wherein the amino acid sequence is selected from the group consisting of LLQRRRL (SEQ ID NO: 14), LRQRRL (SEQ ID NO: 26), LKQKKKL (SEQ ID NO: 15), LRQRRDL (SEQ ID NO: 36), LLQKKKL (SEQ ID NO: 38), LKQKKL (SEQ ID NO: 39), LRQSSSL (SEQ ID NO: 35), LLQSSSL (SEQ ID NO: 40), LRQSSL (SEQ ID NO: 41), LRQRDDL (SEQ ID NO: 37), LLQRDDL (SEQ ID NO: 42), and LRQRDL (SEQ ID NO: 43).

11. A method for imparting cell permeability to or enhancing cell permeability of a lipid membrane structure, comprising binding a peptide to the lipid\membrane structure, wherein the peptide consists of an amino acid sequence selected from the group consisting of $LX_1X_2X_1X_1X_1L$, $LLX_2X_1X_1X_1L$, LRQRRL (SEQ ID NO: 26), LKQKKL (SEQ ID NO: 39), LRQSSL (SEQ ID NO: 41), and LRQRDL (SEQ ID NO: 43), wherein L represents a leucine residue, R represents an arginine residue, Q represents a glutamine residue, K represents a lysine residue, S represents a serine residue, D represents an aspartic acid residue, T represents a threonine residue, E represents a glutamic acid residue, and N represents an asparagine residue, $X_1$ represents a polar amino acid residue selected from the group consisting of S, T, D, E, R and K, and $X_2$ represents a polar, non-charged and branched chain amino acid residue selected from the group consisting of Q and N, wherein the amino acid sequence does not comprise LRQRRRL (SEQ ID NO: 1), whereby the cell permeability of the lipid membrane structure bound to the peptide is imparted or enhanced as compared with the lipid membrane not bound to the peptide, wherein the peptide is bound to a lipid molecule in the lipid membrane structure and wherein the peptide is further covalently bound to a tyrosine residue, a cysteine residue and a hydrophilic polymer in that physical order to the C-terminal end of the peptide.

12. The method according to claim 7, wherein the cell is an epithelial cell.

13. The method of claim 1, wherein $X_1$ is selected from the group consisting of R, K, S and D, and wherein $X_2$ is Q.

14. The method of claim 1, wherein the amino acid sequence is selected from the group consisting of LLQRRRL (SEQ ID NO: 14), LKQKKKL (SEQ ID NO: 15), LRQSSSL (SEQ ID NO: 35), LRQRRDL (SEQ ID NO: 36) and LRQRDDL (SEQ ID NO: 37).

15. The method of claim 7, wherein $X_1$ is selected from the group consisting of R, K, S and D, and wherein $X_2$ is Q.

16. The method of claim 7, wherein the amino acid sequence is selected from the group consisting of LLQRRRL (SEQ ID NO: 14), LKQKKKL (SEQ ID NO: 15), LRQSSSL (SEQ ID NO: 35), LRQRRDL (SEQ ID NO: 36) and LRQRDDL (SEQ ID NO: 37).

* * * * *

SEQUENCE LISTING

<160> NUMBER OF SEQ ID NOS: 43

<210> SEQ ID NO 1
<211> LENGTH: 7
<212> TYPE: PRT
<213> ORGANISM: Artificial
<220> FEATURE:
<223> OTHER INFORMATION: chemically-synthesized peptide, cell-
      penetrating peptide

<400> SEQUENCE: 1

Leu Arg Gln Arg Arg Arg Leu
1               5

<210> SEQ ID NO 2
<211> LENGTH: 7
<212> TYPE: PRT
<213> ORGANISM: Artificial
<220> FEATURE:
<223> OTHER INFORMATION: chemically-synthesized peptide

<400> SEQUENCE: 2

Arg Lys Arg Ile Arg Met Arg
1               5

<210> SEQ ID NO 3
<211> LENGTH: 7
<212> TYPE: PRT
<213> ORGANISM: Artificial
<220> FEATURE:
<223> OTHER INFORMATION: chemically-synthesized peptide

<400> SEQUENCE: 3

Arg Arg Arg Arg Gln Asn Ile
1               5

<210> SEQ ID NO 4
<211> LENGTH: 7
<212> TYPE: PRT
<213> ORGANISM: Artificial
<220> FEATURE:
<223> OTHER INFORMATION: chemically-synthesized peptide

<400> SEQUENCE: 4

Arg Lys Arg Ser Arg Met Arg
1               5

<210> SEQ ID NO 5
<211> LENGTH: 7
<212> TYPE: PRT
<213> ORGANISM: Artificial
<220> FEATURE:
<223> OTHER INFORMATION: chemically-synthesized peptide

<400> SEQUENCE: 5

Ile Arg Gln Arg Arg Arg Arg
1               5

<210> SEQ ID NO 6
<211> LENGTH: 8
<212> TYPE: PRT
<213> ORGANISM: Artificial
<220> FEATURE:
<223> OTHER INFORMATION: chemically-synthesized peptide, cell-
      penetrating peptide

<400> SEQUENCE: 6

```
Arg Arg Arg Arg Arg Arg Arg Arg
1               5

<210> SEQ ID NO 7
<211> LENGTH: 8
<212> TYPE: PRT
<213> ORGANISM: Artificial
<220> FEATURE:
<223> OTHER INFORMATION: chemically-synthesized peptide, cell-
      penetrating peptide

<400> SEQUENCE: 7

Lys Lys Lys Lys Lys Lys Lys Lys
1               5

<210> SEQ ID NO 8
<211> LENGTH: 7
<212> TYPE: PRT
<213> ORGANISM: Artificial
<220> FEATURE:
<223> OTHER INFORMATION: chemically-synthesized peptide

<400> SEQUENCE: 8

Arg Arg Gln Arg Arg Arg Leu
1               5

<210> SEQ ID NO 9
<211> LENGTH: 7
<212> TYPE: PRT
<213> ORGANISM: Artificial
<220> FEATURE:
<223> OTHER INFORMATION: chemically-synthesized peptide

<400> SEQUENCE: 9

Leu Arg Gln Arg Arg Arg Arg
1               5

<210> SEQ ID NO 10
<211> LENGTH: 7
<212> TYPE: PRT
<213> ORGANISM: Artificial
<220> FEATURE:
<223> OTHER INFORMATION: chemically-synthesized peptide

<400> SEQUENCE: 10

Arg Arg Gln Arg Arg Arg Arg
1               5

<210> SEQ ID NO 11
<211> LENGTH: 7
<212> TYPE: PRT
<213> ORGANISM: Artificial
<220> FEATURE:
<223> OTHER INFORMATION: chemically-synthesized peptide

<400> SEQUENCE: 11

Ser Arg Gln Arg Arg Arg Ser
1               5

<210> SEQ ID NO 12
<211> LENGTH: 7
<212> TYPE: PRT
<213> ORGANISM: Artificial
<220> FEATURE:
<223> OTHER INFORMATION: chemically-synthesized peptide

<400> SEQUENCE: 12
```

```
Ile Arg Gln Arg Arg Arg Ile
1               5

<210> SEQ ID NO 13
<211> LENGTH: 7
<212> TYPE: PRT
<213> ORGANISM: Artificial
<220> FEATURE:
<223> OTHER INFORMATION: chemically-synthesized peptide

<400> SEQUENCE: 13

Val Arg Gln Arg Arg Arg Val
1               5

<210> SEQ ID NO 14
<211> LENGTH: 7
<212> TYPE: PRT
<213> ORGANISM: Artificial
<220> FEATURE:
<223> OTHER INFORMATION: chemically-synthesized peptide, cell-
      penetrating peptide

<400> SEQUENCE: 14

Leu Leu Gln Arg Arg Arg Leu
1               5

<210> SEQ ID NO 15
<211> LENGTH: 7
<212> TYPE: PRT
<213> ORGANISM: Artificial
<220> FEATURE:
<223> OTHER INFORMATION: chemically-synthesized peptide, cell-
      penetrating peptide

<400> SEQUENCE: 15

Leu Lys Gln Lys Lys Lys Leu
1               5

<210> SEQ ID NO 16
<211> LENGTH: 8
<212> TYPE: PRT
<213> ORGANISM: Artificial
<220> FEATURE:
<223> OTHER INFORMATION: chemically-synthesized peptide

<400> SEQUENCE: 16

Leu Arg Arg Gln Arg Arg Arg Leu
1               5

<210> SEQ ID NO 17
<211> LENGTH: 9
<212> TYPE: PRT
<213> ORGANISM: Artificial
<220> FEATURE:
<223> OTHER INFORMATION: chemically-synthesized peptide

<400> SEQUENCE: 17

Leu Arg Arg Arg Gln Arg Arg Arg Leu
1               5

<210> SEQ ID NO 18
<211> LENGTH: 7
<212> TYPE: PRT
<213> ORGANISM: Artificial
<220> FEATURE:
<223> OTHER INFORMATION: chemically-synthesized peptide

<400> SEQUENCE: 18
```

```
Leu Arg Arg Arg Arg Arg Leu
1               5

<210> SEQ ID NO 19
<211> LENGTH: 7
<212> TYPE: PRT
<213> ORGANISM: Artificial
<220> FEATURE:
<223> OTHER INFORMATION: chemically-synthesized peptide

<400> SEQUENCE: 19

Leu Arg Ala Arg Arg Arg Leu
1               5

<210> SEQ ID NO 20
<211> LENGTH: 7
<212> TYPE: PRT
<213> ORGANISM: Artificial
<220> FEATURE:
<223> OTHER INFORMATION: chemically-synthesized peptide

<400> SEQUENCE: 20

Leu Arg Arg Gln Arg Arg Leu
1               5

<210> SEQ ID NO 21
<211> LENGTH: 7
<212> TYPE: PRT
<213> ORGANISM: Artificial
<220> FEATURE:
<223> OTHER INFORMATION: chemically-synthesized peptide

<400> SEQUENCE: 21

Leu Arg Arg Arg Gln Arg Leu
1               5

<210> SEQ ID NO 22
<211> LENGTH: 9
<212> TYPE: PRT
<213> ORGANISM: Artificial
<220> FEATURE:
<223> OTHER INFORMATION: chemically-synthesized peptide

<400> SEQUENCE: 22

Leu Leu Arg Gln Arg Arg Arg Leu Leu
1               5

<210> SEQ ID NO 23
<211> LENGTH: 9
<212> TYPE: PRT
<213> ORGANISM: Artificial
<220> FEATURE:
<223> OTHER INFORMATION: chemically-synthesized peptide

<400> SEQUENCE: 23

Arg Leu Arg Gln Arg Arg Arg Leu Arg
1               5

<210> SEQ ID NO 24
<211> LENGTH: 7
<212> TYPE: PRT
<213> ORGANISM: Artificial
<220> FEATURE:
<223> OTHER INFORMATION: chemically-synthesized peptide

<400> SEQUENCE: 24
```

Gln Arg Arg Leu Leu Arg Arg
1               5

<210> SEQ ID NO 25
<211> LENGTH: 7
<212> TYPE: PRT
<213> ORGANISM: Artificial
<220> FEATURE:
<223> OTHER INFORMATION: chemically-synthesized peptide

<400> SEQUENCE: 25

Arg Arg Leu Leu Gln Arg Arg
1               5

<210> SEQ ID NO 26
<211> LENGTH: 6
<212> TYPE: PRT
<213> ORGANISM: Artificial
<220> FEATURE:
<223> OTHER INFORMATION: chemically-synthesized peptide, cell-
      penetrating peptide

<400> SEQUENCE: 26

Leu Arg Gln Arg Arg Leu
1               5

<210> SEQ ID NO 27
<211> LENGTH: 5
<212> TYPE: PRT
<213> ORGANISM: Artificial
<220> FEATURE:
<223> OTHER INFORMATION: chemically-synthesized peptide

<400> SEQUENCE: 27

Leu Arg Gln Arg Leu
1               5

<210> SEQ ID NO 28
<211> LENGTH: 8
<212> TYPE: PRT
<213> ORGANISM: Artificial
<220> FEATURE:
<223> OTHER INFORMATION: chemically-synthesized peptide

<400> SEQUENCE: 28

Leu Arg Gln Arg Arg Arg Arg Leu
1               5

<210> SEQ ID NO 29
<211> LENGTH: 9
<212> TYPE: PRT
<213> ORGANISM: Artificial
<220> FEATURE:
<223> OTHER INFORMATION: chemically-synthesized peptide

<400> SEQUENCE: 29

Leu Arg Gln Arg Arg Arg Arg Arg Leu
1               5

<210> SEQ ID NO 30
<211> LENGTH: 8
<212> TYPE: PRT
<213> ORGANISM: Artificial
<220> FEATURE:
<223> OTHER INFORMATION: chemically-synthesized peptide

<400> SEQUENCE: 30

```
Leu Arg Gln Arg Arg Arg Leu Leu
1               5

<210> SEQ ID NO 31
<211> LENGTH: 8
<212> TYPE: PRT
<213> ORGANISM: Artificial
<220> FEATURE:
<223> OTHER INFORMATION: chemically-synthesized peptide

<400> SEQUENCE: 31

Leu Arg Gln Arg Arg Arg Ala Leu
1               5

<210> SEQ ID NO 32
<211> LENGTH: 9
<212> TYPE: PRT
<213> ORGANISM: Artificial
<220> FEATURE:
<223> OTHER INFORMATION: chemically-synthesized peptide

<400> SEQUENCE: 32

Leu Arg Gln Arg Arg Arg Ala Ala Leu
1               5

<210> SEQ ID NO 33
<211> LENGTH: 7
<212> TYPE: PRT
<213> ORGANISM: Artificial
<220> FEATURE:
<223> OTHER INFORMATION: chemically-synthesized peptide

<400> SEQUENCE: 33

Leu Arg Gln Arg Leu Arg Leu
1               5

<210> SEQ ID NO 34
<211> LENGTH: 7
<212> TYPE: PRT
<213> ORGANISM: Artificial
<220> FEATURE:
<223> OTHER INFORMATION: chemically-synthesized peptide

<400> SEQUENCE: 34

Leu Arg Gln Leu Arg Arg Leu
1               5

<210> SEQ ID NO 35
<211> LENGTH: 7
<212> TYPE: PRT
<213> ORGANISM: Artificial
<220> FEATURE:
<223> OTHER INFORMATION: chemically-synthesized peptide, cell-
      penetrating peptide

<400> SEQUENCE: 35

Leu Arg Gln Ser Ser Ser Leu
1               5

<210> SEQ ID NO 36
<211> LENGTH: 7
<212> TYPE: PRT
<213> ORGANISM: Artificial
<220> FEATURE:
<223> OTHER INFORMATION: chemically-synthesized peptide

<400> SEQUENCE: 36
```

Leu Arg Gln Arg Arg Asp Leu
1               5

<210> SEQ ID NO 37
<211> LENGTH: 7
<212> TYPE: PRT
<213> ORGANISM: Artificial
<220> FEATURE:
<223> OTHER INFORMATION: chemically-synthesized peptide, cell-
      penetrating peptide

<400> SEQUENCE: 37

Leu Arg Gln Arg Asp Asp Leu
1               5

<210> SEQ ID NO 38
<211> LENGTH: 7
<212> TYPE: PRT
<213> ORGANISM: Artificial
<220> FEATURE:
<223> OTHER INFORMATION: cell-penetrating peptide

<400> SEQUENCE: 38

Leu Leu Gln Lys Lys Lys Leu
1               5

<210> SEQ ID NO 39
<211> LENGTH: 6
<212> TYPE: PRT
<213> ORGANISM: Artificial
<220> FEATURE:
<223> OTHER INFORMATION: cell-penetrating peptide

<400> SEQUENCE: 39

Leu Lys Gln Lys Lys Leu
1               5

<210> SEQ ID NO 40
<211> LENGTH: 7
<212> TYPE: PRT
<213> ORGANISM: Artificial
<220> FEATURE:
<223> OTHER INFORMATION: cell-penetrating peptide

<400> SEQUENCE: 40

Leu Leu Gln Ser Ser Ser Leu
1               5

<210> SEQ ID NO 41
<211> LENGTH: 6
<212> TYPE: PRT
<213> ORGANISM: Artificial
<220> FEATURE:
<223> OTHER INFORMATION: cell-penetrating peptide

<400> SEQUENCE: 41

Leu Arg Gln Ser Ser Leu
1               5

<210> SEQ ID NO 42
<211> LENGTH: 7
<212> TYPE: PRT
<213> ORGANISM: Artificial
<220> FEATURE:
<223> OTHER INFORMATION: cell-penetrating peptide

<400> SEQUENCE: 42

```
Leu Leu Gln Arg Asp Asp Leu
1               5
```

<210> SEQ ID NO 43
<211> LENGTH: 6
<212> TYPE: PRT
<213> ORGANISM: Artificial
<220> FEATURE:
<223> OTHER INFORMATION: cell-penetrating peptide

<400> SEQUENCE: 43

```
Leu Arg Gln Arg Asp Leu
1               5
```